US008361310B2

(12) United States Patent
Etter et al.

(10) Patent No.: US 8,361,310 B2
(45) Date of Patent: Jan. 29, 2013

(54) SYSTEM AND METHOD OF INTRODUCING AN ADDITIVE WITH A UNIQUE CATALYST TO A COKING PROCESS

(76) Inventors: Roger G. Etter, Delaware, OH (US); Augusto Quinones, Houston, TX (US)

( * ) Notice: Subject to any disclaimer, the term of this patent is extended or adjusted under 35 U.S.C. 154(b) by 366 days.

(21) Appl. No.: 12/372,586

(22) Filed: Feb. 17, 2009

(65) Prior Publication Data
US 2009/0209799 A1    Aug. 20, 2009

Related U.S. Application Data

(63) Continuation-in-part of application No. 12/371,909, filed on Feb. 16, 2009, which is a continuation-in-part of application No. 12/377,188, filed as application No. PCT/US2007/085111 on Nov. 19, 2007.

(60) Provisional application No. 61/028,785, filed on Feb. 14, 2008, provisional application No. 60/866,345, filed on Nov. 17, 2006.

(51) Int. Cl.
*C10B 55/00* (2006.01)
(52) U.S. Cl. ............ 208/52 R; 208/50; 208/51; 208/53; 208/54; 208/55; 208/131
(58) Field of Classification Search .................... 208/50, 208/52 R, 53–55, 131, 52 CT, 67–77
See application file for complete search history.

(56) References Cited

U.S. PATENT DOCUMENTS

| | | | |
|---|---|---|---|
| 1,831,719 A | 11/1931 | Pelzer | |
| 1,873,024 A | 8/1932 | Pelzer | |
| RE20,011 E | 6/1936 | Pelzer | |
| 2,881,130 A | 4/1959 | Pfeiffer et al. | |
| 2,905,622 A | 9/1959 | McCarthy | |
| 2,922,755 A | 1/1960 | Hackley, Jr. | |
| 3,382,084 A | 5/1968 | Folkins et al. | |
| 3,617,480 A | 11/1971 | Keel | |
| 3,661,543 A | 5/1972 | Saxton | |
| 3,684,697 A | 8/1972 | Gamson | |
| 3,702,516 A | 11/1972 | Luckenbach | |

(Continued)

FOREIGN PATENT DOCUMENTS
DE    19540780    5/1996

OTHER PUBLICATIONS

Fletcher, Peter, Delayed Coking, Chem. Engineer, Sep./Oct. 1983, 21-23.

(Continued)

*Primary Examiner* — Brian McCaig
(74) *Attorney, Agent, or Firm* — Standley Law Group LLP

(57) ABSTRACT

Gas oil components, coking process recycle, and heavier hydrocarbons are cracked or coked in the coking vessel by injecting an additive into the vapors of traditional coking processes in the coking vessel. The additive contains catalyst(s), seeding agent(s), excess reactant(s), quenching agent(s), carrier(s), or any combination thereof to modify reaction kinetics to preferentially crack or coke these components. Modifications of the catalysts in the additive improve performance for certain desired outcomes. One exemplary embodiment of the present invention uses the olefin production capabilities from newly developed catalysts to increase the production of light olefins (e.g. ethylene, propylenes, butylenes, pentenes) for alkylation process unit feed, the production of oxygenates, and petrochemical feedstocks, such as plastics manufacture. Another exemplary embodiment of the present invention is the use of the olefin production from newly developed catalysts to improve the coker naphtha quality. A third exemplary embodiment of the present invention uses the cracking characteristics of newly developed catalysts to optimize the production of light gas oils, naphtha, and gases from the coking process.

9 Claims, 5 Drawing Sheets

U.S. PATENT DOCUMENTS

Figure 1:
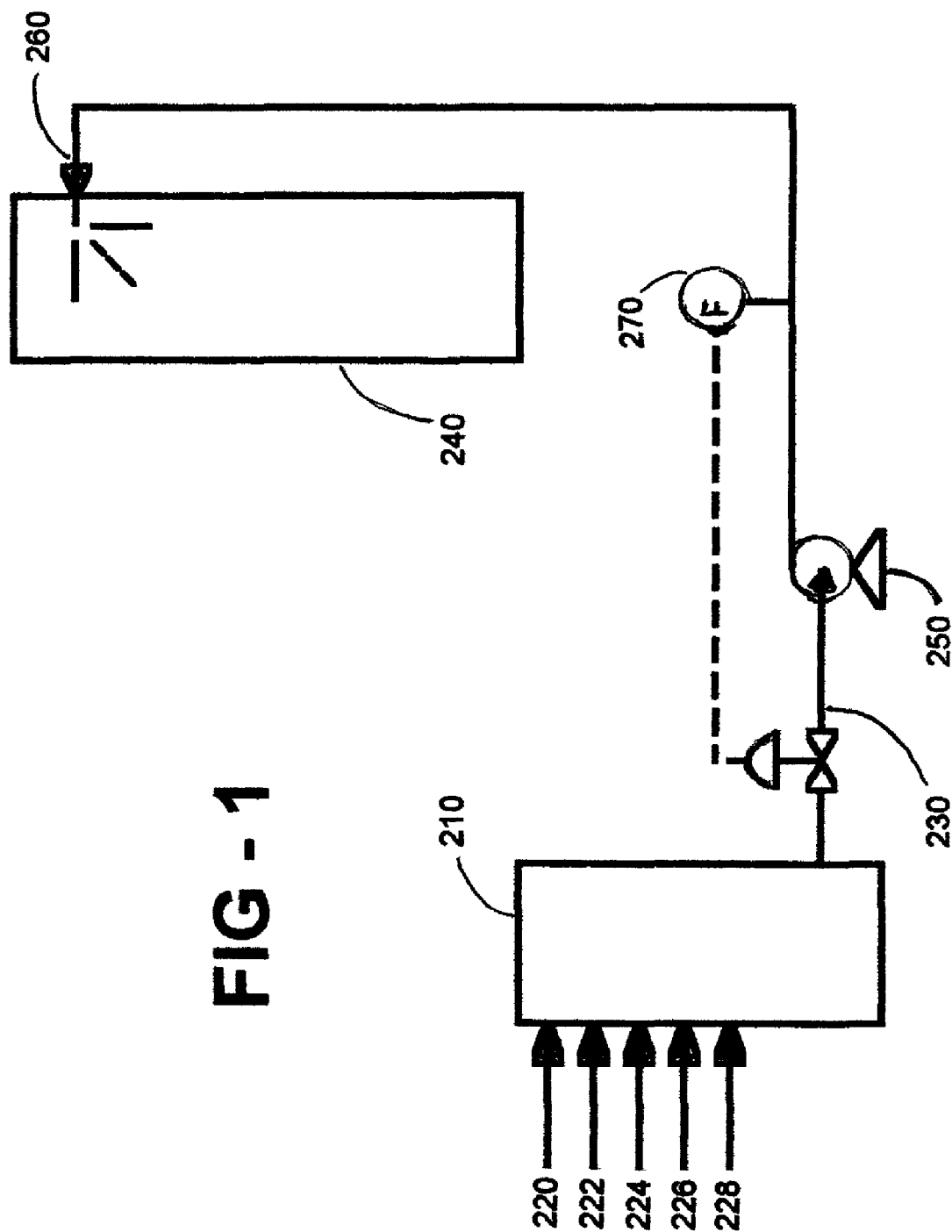

| | | |
|---|---|---|
| 3,702,816 A | 11/1972 | Buchmann et al. |
| 3,759,676 A | 9/1973 | Lahn |
| 3,775,290 A | 11/1973 | Peterson et al. |
| 3,775,294 A | 11/1973 | Peterson et al. |
| 3,816,084 A | 6/1974 | Moser, Jr. et al. |
| 3,842,165 A | 10/1974 | Grindstaff et al. |
| 3,852,047 A | 12/1974 | Schlinger et al. |
| 3,896,023 A | 7/1975 | Ozaki et al. |
| 3,917,564 A | 11/1975 | Meyers |
| 3,932,587 A | 1/1976 | Grantham et al. |
| 3,960,701 A | 6/1976 | Schroeder |
| 4,043,898 A | 8/1977 | Kegler |
| 4,049,538 A | 9/1977 | Hayashi et al. |
| 4,055,484 A | 10/1977 | Blaser et al. |
| 4,096,097 A | 6/1978 | Yan |
| 4,100,035 A | 7/1978 | Smith |
| 4,178,229 A | 12/1979 | McConaghy et al. |
| 4,188,277 A | 2/1980 | Martin |
| 4,198,380 A | 4/1980 | Kohl |
| 4,202,868 A | 5/1980 | Hayashi et al. |
| 4,269,696 A | 5/1981 | Metrailer |
| 4,291,008 A | 9/1981 | Hsu et al. |
| 4,295,956 A | 10/1981 | Metrailer |
| 4,302,324 A | 11/1981 | Chen et al. |
| 4,312,742 A | 1/1982 | Hayashi |
| 4,326,853 A | 4/1982 | Sze et al. |
| 4,334,980 A | 6/1982 | Hsu |
| 4,364,741 A | 12/1982 | Villa |
| 4,369,171 A | 1/1983 | Grindstaff et al. |
| 4,388,152 A | 6/1983 | Wasson et al. |
| 4,406,872 A | 9/1983 | Kapner et al. |
| 4,441,887 A | 4/1984 | Funk |
| 4,443,415 A | 4/1984 | Queneau et al. |
| 4,447,259 A | 5/1984 | Ohyama et al. |
| 4,455,219 A | 6/1984 | Janssen et al. |
| 4,478,602 A | 10/1984 | Kelley et al. |
| 4,479,804 A | 10/1984 | Chen et al. |
| 4,481,101 A | 11/1984 | Yan |
| 4,490,171 A | 12/1984 | Suzuki et al. |
| 4,498,976 A | 2/1985 | Degnan et al. |
| 4,518,486 A | 5/1985 | Jansma |
| 4,519,898 A | 5/1985 | Allan |
| 4,521,277 A | 6/1985 | Calderon et al. |
| 4,534,951 A | 8/1985 | Kortovich et al. |
| 4,547,284 A | 10/1985 | Sze et al. |
| 4,551,232 A | 11/1985 | Calderon et al. |
| 4,631,025 A | 12/1986 | Casper et al. |
| 4,666,585 A | 5/1987 | Figgins et al. |
| 4,797,197 A | 1/1989 | Mallari |
| 4,828,680 A | 5/1989 | Green et al. |
| 4,853,106 A | 8/1989 | Grove et al. |
| 4,874,505 A | 10/1989 | Bartilucci et al. |
| 4,895,636 A | 1/1990 | Chen et al. |
| 5,007,987 A | 4/1991 | Block et al. |
| 5,009,767 A | 4/1991 | Bartilucci et al. |
| 5,015,362 A | 5/1991 | Chin |
| 5,034,030 A | 7/1991 | Miller et al. |
| 5,110,448 A | 5/1992 | Adams et al. |
| 5,114,564 A | 5/1992 | Goyal |
| 5,114,566 A | 5/1992 | Naeger et al. |
| 5,165,902 A | 11/1992 | Bortz et al. |
| 5,174,891 A | 12/1992 | Becraft |
| 5,215,557 A | 6/1993 | Johnson et al. |
| 5,246,680 A | 9/1993 | Esa |
| 5,258,115 A | 11/1993 | Heck et al. |
| 5,259,864 A | 11/1993 | Greenwalt |
| 5,277,795 A | 1/1994 | Thornhill et al. |
| 5,339,755 A | 8/1994 | Smith |
| 5,350,503 A | 9/1994 | Freymeyer et al. |
| 5,439,658 A | 8/1995 | Johnson et al. |
| 5,470,556 A | 11/1995 | Samish |
| 5,490,918 A | 2/1996 | Meek |
| 5,496,729 A | 3/1996 | Monticello |
| 5,529,599 A | 6/1996 | Calderon |
| 5,591,326 A | 1/1997 | Shih |
| 5,635,149 A | 6/1997 | Klingspor et al. |
| 5,651,948 A | 7/1997 | Myers et al. |
| 5,954,949 A | 9/1999 | Ohsol et al. |
| 6,024,863 A | 2/2000 | LeCours et al. |
| 6,056,882 A | 5/2000 | Scalliet |
| 6,168,709 B1 | 1/2001 | Etter |
| 6,251,307 B1 | 6/2001 | Lecours et al. |
| 7,037,408 B2 | 5/2006 | Wilborn |
| 7,438,786 B2 | 10/2008 | Malsbury |
| 2001/0006156 A1 | 7/2001 | Pereira et al. |
| 2002/0179493 A1* | 12/2002 | Etter ............................ 208/131 |
| 2004/0173504 A1 | 9/2004 | Klasnich |
| 2006/0032788 A1 | 2/2006 | Etter |
| 2006/0060506 A1 | 3/2006 | Siskin et al. |
| 2009/0145810 A1 | 6/2009 | Etter |
| 2009/0152165 A1 | 6/2009 | Etter |
| 2010/0170827 A1 | 7/2010 | Etter |

OTHER PUBLICATIONS

Janssen et al., Improved Coking Design Can Up Liquid Yields, Oil & Gas J. (Jun. 25, 1984) 79-83.
Lieberman, Norman, Shot Coke: Its Origins and Prevention, Oil & Gas J. (Jul. 8, 1985) 45-46.
Lieberman, Norman, Good Operating Techniques Improve Coker Yield, Increase Gas-Oil Production, Oil & Gas J. (Mar. 10, 1986) 53-54.
Lieberman, Norman, Procedure Reduces Coke Cutting Time for Large Drums, Gas & Oil J. (Nov. 24, 1986) 85-86.
Barnett, Jack, Desalters Can Remove More Than Salts and Sediment, Oil & Gas J. (Apr. 11, 1988) 43-49.
Archuletta et al., Cooperative Corrosion Control and Treatment Program Proves Effective, Gas & Oil J. (Aug. 6, 1990) 60-68.
Elliott, John, Design Operation Factors Can Up Coker Liquid Yields, Gas & Oil J. (Feb. 4, 1991) 41-44.
Filtration Method Efficiently Desalts Crude in Commercial Test, Gas & Oil J. (May 17, 1993) 59-60.
Bansal et al., Improve Your Coking Process, Hydrocarbon Processing (Feb. 1994) 63-66.
Stefani, A., Debottleneck Delayed Cokers for Greater Profitability, Hydorcarbon Processing (Jun. 1996) 99-103.
Harris, J.R., Use Desalting for FCC Feedstocks, Hydrocarbon Processing (Aug. 1996) 63-68.
Dickenson, et al., Refiner Options for Converting and Utilizing Heavy Fuel Oil, Hydrocarbon Processing (Feb. 1997) 57-62.
Auxiliary Equipment, Corrosion Focus of Refining Meeting, Oil & Gas J. (Apr. 4, 1994).
Wagoner et al., Burning Profiles for Solid Fuels, Amer. Soc. Mech. Eng. (Aug. 7, 1967) 1-8.
Reid, William, Ash Chemistry and Its Effect in Broiler Furnaces, Elec. Power Res. Inst. (Dec. 2, 1980) 1-13.
Burning Petroleum Coke: Boiler/Complex FGD or Fluid-Bed Combustor?, (Jul. 7, 1983).
Lieberman, Norman, Time for Coking Cycle Can Be Routinely Halved, Oil & Gas J. (Aug. 29, 1983) 39-44.
Delayed Coking, Hydrocarbon Processing (Sep. 1984) 113.
Kronenberger et al., Troubleshooting the Refinery Desalter Operation, Materials Performance (Jul. 1986) 9-17.
Muzio et al., Dry Sorbent Emission Control Technologies, JAPC Assoc. (May 1987) 642-654.
Deepwater Fires 100% Coke, Sells All FGD Gypsoum Product, Power (Oct. 1988).
Lieberman, Norman, Frequently Asked Questions on Coke Quality Answered, Oil & Gas J. (Mar. 27, 1989) 67-69.
Makansi, Jason, Clean Air Act Amendments: The Engineering Response, Power (Jun. 1991) 11-60.
Herzog et al., Feasibility, Modeling and Economics of Sequestering Power Plant CO2 Emissions in the Deep Ocean, Envior. Progress vol. 10 (Feb. 1991) 64-74.
Elliott, J.D., Maximize Distillate Liquid Products, Hydrocarbon Proc. (Jan. 1992) 75-80.
Sulfur Dioxide Control, Steam 40 (1992) Chapter 35.
Fuel Ash Effects on Boiler Design and Operation, Steam 40 (1992) Chapter 20(pp. 1-28).
Sources of Chemical Energy, Steam 40 (1992) Chapter 8.
Burners and Combustion Systems for Pulverized Coal, Steam 40 (1992) Chapter 13.

Kent, James, Handbook of Industrial Chemistry, Published by Van Norstrand Reinhold (1992).

Rittenhouse, R.C., Action Builds on the Road to CAA Compliance (Part II), Power Eng. (Jun. 1992) 43-50.

Batra et al, Desing Process Equipment for Corrosion Control, Chem. Eng. Prog. (May 1993) 68-76.

Livengood et al., FG Technologies for Combined Control of SO2 and NOX, Power Eng. (Jan. 1994) 38-42.

Torrens et al., Electric Utility Response to the Clean Air Act Amendments, Power Eng. (Jan. 1994) 43-47.

Coke Quality, Oil & Gas J. (May 2, 1994) 114-115.

Wolsky et al, CO2 Capture From the Flue Gas of Conventional Fossil-Fuel-Fired Power Plants, Envr. Progress vol. 13 (Aug. 1994) 214-219.

Chue et al., Comparison of Activated Carbon and Zeolite 13X for CO2 Recovery From Flue Gas by Pressure Swing Adsorption, Amer. Chem. Soc. (1995) 591-598.

Akai et al., Performance Evaluation of Fossil Power Plant With CO2 Recovery and Sequestering System, Energy Conyers. Mgmt. vol. 36 Nos. 6-9(1995) 801-804.

Coking/Catalytic Cracking/Catalytic Reforming, HydroCarbon Processing (Oct. 1996).

Refining 1996, HydroCarbon (Nov. 1996).

Sincero & G.A. Sincero, Environmental Engineering a Design Approach, Types of Control (625-633), 1995.

Bisio & A. Boots, Air Pollution Control Methods, The Wiley Encyclopedia Energy and the Environment (vol. 1), 85-91, 1996.

Kiely, Gerard, Environmental Engineering, (344-345) & (757-776), 1998.

Handbook of Petroleum Refining Processes, (Jul. 16-29, 2003).

Delayed Coking, Chapter 5 (52-64).

Kirk-Othmer Ency. of Chem. Tehc. 3rd Ed., vol. 17 (194-219), 1978.

Kirk-Othmer Ency. of Chem Tech., 4th Ed., vol. 18 (433-469), 2001.

Ency. of Chem. Processing and Design, vol. 10 (1-41), 1980.

U.S. Department of Energy, DOE Techline Fossil Energy, New Research Focuses on Reducing Energy Consumption, Improving Environmental Performance of Refinery Coking Process, 2 pp., (Apr. 22, 1999).

W.R. Grace & Co.-Conn., Guide to Fluid Catalytic Cracking Part Two, copyright 1996, 98 pages.

Ellis, Paul J. and Paul A. Christopher, Tutorial: Delayed Coking Fundamentals, Great Lakes Carbon Corporation, Prepared for presentation at the AIChE 1998 Spring National Meeting Mar. 8-12, 1998, 20 pages.

\* cited by examiner

SYSTEM AND METHOD OF INTRODUCING AN ADDITIVE WITH A UNIQUE CATALYST TO A COKING PROCESS

This application claims priority to U.S. Provisional Application No. 61/028,785, filed Feb. 14, 2008, which is hereby incorporated by reference in its entirety. This application is also a continuation-in-part of U.S. application Ser. No. 12/371,909, filed Feb. 16, 2009, which is a continuation-in-part of U.S. application Ser. No. 12/377,188, filed Feb. 11, 2009, which claims priority to PCT Application No. PCT/US2007/085111, filed Nov. 19, 2007, which claims priority to U.S. Provisional Application No. 60/866,345, filed Nov. 17, 2006, each of which is hereby incorporated by reference in its entirety.

BACKGROUND

1. Field of the Invention

This invention relates generally to the field of thermal coking processes, and more specifically to modifications of petroleum refining thermal coking processes to improve the product yields and/or the characteristics of the products of the coking process. Exemplary embodiments of the invention also relate generally to the production of various types of petroleum coke with unique characteristics for fuel, anode, electrode, or other specialty carbon products and markets. Furthermore, this invention relates to the development of catalysts to improve performance.

2. Description of Known Art

Thermal coking processes have been developed since the 1930s to help crude oil refineries process the "bottom of the barrel." In general, modern thermal coking processes employ high-severity, thermal decomposition (or "cracking") to maximize the conversion of very heavy, low-value residuum feeds to lower boiling hydrocarbon products of higher value. Feedstocks for these coking processes normally consist of refinery process streams which cannot economically be further distilled, catalytically cracked, or otherwise processed to make fuel-grade blend streams. Typically, these materials are not suitable for catalytic operations because of catalyst fouling and/or deactivation by ash and metals. Common coking feedstocks include atmospheric distillation residuum, vacuum distillation residuum, catalytic cracker residual oils, hydrocracker residual oils, and residual oils from other refinery units.

There are three major types of modern coking processes currently used in crude oil refineries (and upgrading facilities) to convert the heavy crude oil fractions (or bitumen from shale oil or tar sands) into lighter hydrocarbons and petroleum coke: delayed coking, fluid coking, and flexicoking. These thermal coking processes are familiar to those skilled in the art. In all three of these coking processes, the petroleum coke is considered a by-product that is tolerated in the interest of more complete conversion of refinery residues to lighter hydrocarbon compounds, referred to as 'cracked liquids' throughout this discussion. These cracked liquids range from pentanes to complex hydrocarbons with boiling ranges typically between 350 and 950 degrees F. In all three of these coking processes, the 'cracked liquids' and other products move from the coking vessel to the fractionator in vapor form. The heavier cracked liquids (e.g. gas oils) are commonly used as feedstocks for further refinery processing (e.g. Fluid Catalytic Cracking Units or FCCUs) that transforms them into transportation fuel blend stocks.

Crude oil refineries have regularly increased the use of heavier crudes in their crude blends due to greater availability and lower costs. These heavier crudes have a greater proportion of the "bottom of the barrel" components, increasing the need for coker capacity. Thus, the coker often becomes the bottleneck of the refinery that limits refinery throughput. Also, these heavier crudes often contain higher concentrations of large, aromatic structures (e.g. asphaltenes and resins) that contain greater concentrations of sulfur, nitrogen, and heavy metals, such as vanadium and nickel. As a result, the coking reactions (or mechanisms) are substantially different and tend to produce a denser, shot (vs. sponge) coke crystalline structure (or morphology) with higher concentrations of undesirable contaminants in the pet coke and coker gas oils. Consequently, these three coking processes have evolved through the years with many improvements in their respective technologies.

Many refineries have relied on technology improvements to alleviate the coker bottleneck. Some refineries have modified their vacuum crude towers to maximize the production of vacuum gas oil (e.g. <1050 degree F.) per barrel of crude to reduce the feed (e.g. vacuum reduced crude or VRC) to the coking process and alleviate coker capacity issues. However, this is not generally sufficient and improvements in coker process technologies are often more effective. In delayed coking, technology improvements have focused on reducing cycle times, recycle rates, and/or drum pressure with or without increases in heater outlet temperatures to reduce coke production and increase coker capacity. Similar technology improvements have occurred in the other coking processes, as well.

In addition, coker feedstocks are often modified to alleviate safety issues associated with shot coke production or 'hot spots' or steam 'blowouts' in cutting coke out of the coking vessel. In many cases, decanted slurry oil, heavy cycle oil, and/or light cycle oil from the FCCU are added to the coker feed to increase sponge coke morphology (i.e. reduce shot coke production). This increase in sponge coke is usually sufficient to alleviate the safety problems associated with shot coke (e.g. roll out of drum, plugged drain pipes, etc.). Also, the increase in sponge coke can provide sufficient porosity to allow better cooling efficiency of the quench to avoid 'hot spots' and steam 'blowouts' due to local areas of coke that are not cooled sufficiently before coke cutting. However, the addition of these materials to coker feed reduces coking process capacities.

Unfortunately, many of these technology improvements have substantially decreased the quality of the resulting pet coke. Most of the technology improvements and heavier, sour crudes tend to push the pet coke from porous 'sponge' coke to 'shot' coke (both are terms of the art) with higher concentrations of undesirable impurities: Sulfur, nitrogen, vanadium, nickel, and iron. In some refineries, the shift in coke quality can require a major change in coke markets (e.g. anode to fuel grade) and dramatically decrease coke value. In other refineries, the changes in technology and associated feed changes have decreased the quality of the fuel grade coke with lower volatile matter (VM), gross heating value (GHV), and Hardgrove Grindability Index (GHI). All of these factors have made the fuel grade coke less desirable in the United States, and much of this fuel grade coke is shipped overseas, even with a coal-fired utility boiler on adjacent property. In this manner, the coke value is further decreased.

More importantly, many of these coker technology improvements have substantially reduced the quality of the gas oils that are further processed in downstream catalytic cracking units. That is, the heaviest or highest boiling components of the coker gas oils (often referred to as the 'heavy tail' in the art) are greatly increased in many of these refineries (particularly with heavier, sour crudes). In turn, these increased 'heavy tail' components cause significant reductions in the efficiencies of downstream catalytic cracking units. In many cases, these 'heavy tail' components are primarily polycyclic aromatic hydrocarbons (or PAHs) that have a high propensity to coke and contain much of the remaining, undesirable contaminants of sulfur, nitrogen, and metals. In downstream catalytic cracking units (e.g. FCCUs), these undesirable contaminants of the 'heavy tail' components can significantly increase contaminants in downstream product pools, consume capacities of refinery ammonia recovery/sulfur plants, and increase emissions of sulfur oxides and nitrous oxides from the FCCU regenerator. In addition, these problematic 'heavy tail' components of coker gas oils can significantly deactivate cracking catalysts by increasing coke on catalyst, poisoning of catalysts, and/or blockage or occupation of active catalyst sites. Also, the increase in coke on catalyst can require a more severe regeneration, leading to suboptimal heat balance and catalyst regeneration. Furthermore, the higher severity catalyst regeneration often increases FCCU catalyst attrition, leading to higher catalyst make-up rates, and higher particulate emissions from the FCCU. As a result, not all coker gas oil is created equal. In the past, refinery profit maximization computer models (e.g. Linear Programming Models) in many refineries assumed the same value for gas oil, regardless of quality. This tended to maximize gas oil production in the cokers, even though it caused problems and decreased efficiencies in downstream catalytic cracking units. Some refineries are starting to put vectors in their models to properly devalue these gas oils that reduce the performance of downstream process units.

U.S. Pat. No. 4,394,250 describes a delayed coking process in which small amounts of cracking catalyst and hydrogen are added to the hydrocarbon feedstock before it is charged to the coking drum to increase distillate yield and reduce coke make. The catalyst settles out in the coke and does not affect the utility of the coke.

U.S. Pat. No. 4,358,366 describes a delayed coking process in which small amounts of hydrogen and a hydrogen transfer catalyst, a hydrogenation catalyst, and/or a hydrocracking catalyst are added to a coker feed consisting of shale oil material and a petroleum residuum to enhance yields of liquid product.

Disadvantages of Catalyst with Coker Feed:

This known art adds catalyst to the coker feed, which has substantially different chemical and physical characteristics than the reactants of the current invention. The coker feed of the known art is typically comprised of very heavy aromatics (e.g. asphaltenes, resins, etc.) that have theoretical boiling points greater than 1000° F. As such, the primary reactants exposed to the catalysts of the known art are heavy aromatics with a much higher propensity to coke (vs. crack), particularly with the exposure to high vanadium and nickel content in the coker feed. Furthermore, mineral matter in the coker feed tends to act as a seeding agent that further promotes coking. Calcium, sodium, and iron compounds/particles in the coker feed have been known to increase coking, particularly in the coker feed heater.

From a physical perspective, the primary reactants of the known art are a very viscous liquid (some parts semi-solid) at the inlet to the coker feed heater. Throughout the heater and into the coke drums the feed becomes primarily hot liquid, solids (from feed minerals and coking), and vapors (from coker feed cracking). The temperature of the multi-phase material at the inlet to the drum is typically between 900° F. and 950° F.

In commercial applications of the known art (i.e. catalyst in the delayed coker feed), excessive coking problems have been noted.

UTILITY AND ADVANTAGES OF THE INVENTION

Accordingly, exemplary embodiments of the present invention may (1) improve a quantity of a coker product or the overall yield distributions of coker products, (2) improve a quality or a property of one or more of the coker products, (3) improve operation, maintenance, throughput capacity, efficiency, and/or processing alternatives of the coking process (4) improve the operation, maintenance, throughput capacity, efficiency, and/or processing alternatives for other refinery processing units, and/or (5) provide additional catalytic cracking capacity for a crude oil refinery or upgrading system.

An exemplary embodiment of the present invention can increase or decrease the yield of the various types of coking process products (e.g. cracked liquids, coke, and/or gases). This embodiment of the present invention can effectively use the catalytic additive (by design) to effect an increase or decrease in the various types of desired coking process products, including but not limited to, naphtha, light gas oil, heavy gas oil, liquid petroleum gases (e.g. propanes & butanes), fuel gas, hydrogen, and coke. The catalytic additive can be designed to convert the chemical compounds in the coking process feed or products (intermediate and final) of the thermal cracking and thermal coking reactions of the traditional coking process into other types of chemical compounds or desired products. In this manner, the catalyst characteristics can be modified to perform desired reactions. For example, the catalytic additive added to the coking process can convert chemical compounds in the coking process feed (that would normally form coke in the coking process) into cracked liquids or gas products. Alternatively, the catalytic additive can effectively be used to reduce excess cracking of hydrocarbon vapors (commonly referred to as 'vapor overcracking' in the art) by quenching or catalytically altering such cracking reactions, that convert valuable 'cracked liquids' to less valuable gases (ethanes and lower) that are typically used as fuel (e.g. refinery fuel gas).

Another exemplary embodiment of the present invention can improve the quality of various products of the coking process. In this embodiment, additional components of the feed to the coking process can be catalytically converted by the catalytic additive added to the coking process into cracked liquids and gas products. Alternatives of this exemplary embodiment can use catalysts that are designed for higher selectivity and reactivity toward certain components of the feed to the coking process or products of the thermal cracking and thermal coking of the traditional coking process. For example, the quality of gas oils can be effectively improved by the catalytic additive of exemplary embodiments of the current invention by (1) catalytically cracking various gas oil components to increase lighter cracked liquids or gases and/or (2) catalytically coking them. Depending on the operation of the individual coking process, this selective cracking and/or coking of certain gas oil components can lead to a reduction in coker recycle and/or improve the quality of the coker gas oils. In turn, an improvement in coker gas oil can improve operation and efficiency of downstream processing units, particularly cracking units. Furthermore, exemplary embodiments of the present invention may be used to significantly improve the quality of the petroleum coke. An exemplary embodiment of the present invention may also be used to enhance the quality of the petroleum coke by selective catalytic coking of any components of the feed to the coking process and/or chemical intermediates formed in the coking process. This embodiment of the catalytic coking may be done in a manner that improves the quality of the pet coke for anode, electrode, fuel, or specialty carbon markets. An exemplary embodiment can also increase sponge coke morphology to avoid safety issues associated with shot coke production and 'hot spots' and steam 'blowouts' during coke cutting. In many cases, this can be done by catalytically cracking and/or coking heavy aromatics (e.g. asphaltenes and their derivatives) that otherwise fill and block cooling channels in the coke. Typically, this can be done without using valuable capacity to add slurry oil or other additives to the coker feed to achieve these objectives. Furthermore, an exemplary embodiment of the present invention can reduce shot coke in a manner that may improve coke quality sufficiently to allow sales in the anode coke market.

Other exemplary embodiments of the present invention may be used to improve the operation, maintenance, throughput capacity, efficiency, and/or processing alternatives for the coking process. That is, a catalytic additive may be added to the coking process in a manner that changes the coking process in a positive manner that can improve operation and/or maintenance. For example, a catalytic additive can reduce the chemical compounds that have a high propensity to coke in the coking process heater, vapor line to the fractionator, and other coking process components and reduce operational problems and maintenance issues. In another exemplary embodiment, a catalytic additive can be added to the coking process in a manner that achieves a reduction of pet coke, gas production, and/or coker recycle that can all help to increase the throughput capacity of the coking process. A catalytic additive can also be effectively used to provide other means to debottleneck the coking process. An exemplary embodiment of the present invention may also provide a superior means to increase coking process capacity without sacrificing the quality and quantity of desirable coker products, such as coker gas oil quality. In many cases, the increase in coking capacity also leads to an increase in refinery throughput capacity in refineries where the coking process is the refinery bottleneck. Other exemplary embodiments of the present invention can increase the efficiency of the coking process. For example, a catalytic additive may effectively (1) increase valuable products without additional process severity, (2) decrease required recycle and associated heater fuel per barrel of feed processed, and/or (3) decrease vapor loading to the fractionator, which all increase coking process efficiency. Furthermore, additional exemplary embodiments of the present invention may be used to provide processing alternatives in the coking process, including but not limited to, changing (1) coking process feed quality, (2) gas oil quantity and/or quality, (3) coke quantity and/or quality, and/or (4) quantity and/or quality of gas production.

Other exemplary embodiments of the present invention improve the operation, maintenance, throughput capacity, efficiency, and/or processing alternatives for other refinery processing units. The catalytic additive added to the coking process may be used to improve these by improving the quantity and/or quality of the coking process products that are further processed in downstream refinery processing units. For example, improving the quality of gas oils can increase the efficiency and improve the operation, maintenance, and throughput capacity of the downstream fluid catalytic cracking unit (FCCU), and/or provide the opportunity to process some of these gas oil components in a hydrocracking process. Decreasing the quantity of these gas oils can also provide the opportunity to decrease the process severity of the FCCU and/or provide processing alternatives for other types of FCCU feeds. An exemplary embodiment of the present invention may also allow crude slate flexibility for refineries that want to increase the proportion of heavy, sour crudes without sacrificing coke quality, particularly with refineries that currently produce anode grade coke. Another exemplary embodiment of the current invention improves the quality of the coke in a manner that improves the operation and efficiency of downstream calcining facilities.

Finally, other exemplary embodiments of the present invention can provide additional catalytic cracking capacity for a crude oil refinery (or upgrading systems for shale oil, tar sands, etc.) by achieving cracking of feed components in the coking process beyond the thermal cracking that normally occurs. In some cases, the additional catalytic cracking in the coking process may be sufficient to provide an economic alternative to adding downstream cracking capacity (e.g. fluid catalytic cracking unit or hydrocracker) and/or the addition of feed pretreatment for downstream catalytic cracking.

In summary, the present invention has many exemplary embodiments that can occur somewhat independently, depending on several factors, including the quality and quantity of the catalytic additive. In many cases, however, the exemplary embodiments will overlap and occur concurrently, but to different degrees. As such, the present invention provides the opportunity to develop catalytic additive(s) to address the specific needs of a particular refinery. That is, the catalytic additive(s) can be specifically designed to improve the yield distribution to the products that are most valuable to that refinery's process scheme and crude slate opportunities. This approach may simply involve catalytic cracking to produce greater yields of cracked liquids or may involve more sophisticated catalytic additive to be selective in desired types of cracked liquids. Similarly, an additional catalytic additive could be added to produce more of the desired products at that particular facility (e.g. propylene for local plastics plant) or selectively convert particular types of chemical species in the feed to the coking process or intermediate chemical species in the coking process from other chemical reactions. That is, 'intermediate products' or 'intermediate chemical species' shall refer to chemical species, including coking process products, in the coking process caused by thermal cracking, thermal coking, and various other chemical reactions with the coking process feed components. In this approach, the process optimization model in each refinery could be used as an effective tool in determining what catalytic additives would be preferable and worth pursuing (e.g. cost effectiveness and return on investment). All of the exemplary embodiments of the present invention potentially improve the overall refinery profitability. Further objects and advantages of this invention will become apparent from consideration of the drawings and ensuing descriptions.

SUMMARY OF THE INVENTION

An exemplary embodiment of the present invention is an improvement of coking processes which adds an additive to the coking vessel of a coking process to convert (e.g. via catalytic cracking) intermediate hydrocarbon species (i.e. created by thermal cracking of coker feed) of the coking process to improve the quality and/or value of the products of the coking process. The basic technology contemplated in U.S. Provisional Application No. 60/866,345 uses this additive (often containing catalyst) to crack or coke high boiling point compounds (e.g. heavy coker gas oils). As indicated, 'conversion includes cracking these high boiling point compounds to lighter hydrocarbons,' including 'naphtha, gas oil, gasoline, kerosene, jet fuel, diesel fuel, & heating oil.' In U.S. application Ser. No. 12/377,188, various other exemplary embodiments are discussed, including the use of the additive (with or without catalyst) as a quenching agent to reduce vapor overcracking reactions. Much discussion is devoted to what is considered one of the best modes of operation for the present invention, which uses the additive (with catalyst) to selectively convert (preferably cracking) the highest boiling point materials in the product vapors of the coking process to minimize the coker recycle and/or significantly improve the quality of the heavy coker gas oil. By converting these problematic components to lighter liquid products and/or higher quality petroleum coke, this embodiment of the present invention potentially provides the greatest upgrade in value for the coking process: (1) increasing liquid yields, while decreasing coke yields, (2) minimizing coker recycle by creating an 'internal recycle,' (3) improving quality of coker gas oil and/or petroleum coke, (3) reducing 'vapor overcracking' and associated loss of liquids to lower value gases, (4) reducing 'hotspots' and/or 'blowouts' & associated safety issues and costs, (5) increasing coker capacity and potentially refinery capacity, (6) increasing crude slate flexibility, and/or (7) improving operation & maintenance of the coking process and downstream processing units.

In this Continuation-in-Part (CIP), further information is provided to help differentiate the present invention over known art, including comparative data from pilot plant tests. In these pilot plant tests, the injection of the catalyst additive into the coking vessel of the current invention and the addition of catalyst to the coker feed of the known art were compared to a common baseline with no catalyst. In two set of test data, the catalyst addition of the known art showed a substantial increase in coking and a significant reduction in liquid yields. In contrast, the injection of the catalytic additive of the present invention showed a substantial reduction in coke yield and a significant increase in liquids production. Thus, these tests clearly demonstrate differentiation of the present invention over the known art. These results are likely due to the major differences in the chemical and physical nature of the primary reactants, exposed to the catalyst in the known art versus the current invention. Further analyses are provided in this regard. Finally, improvements to exemplary embodiments of the present invention in U.S. application Ser. No. 12/377,188 are discussed relative to modifications of the catalysts in the additive to improve performance for certain desired outcomes. One exemplary embodiment of the present invention uses the olefin production capabilities from newly developed and/or existing types of catalysts to increase the production of light olefins (e.g. ethylene, propylenes, butylenes, pentenes) for alkylation process unit feed, the production of oxygenates, and petrochemical feedstocks, such as plastics manufacture. Another exemplary embodiment of the present invention is the use of the olefin production from newly developed and/or existing types of catalysts to improve the coker naphtha quality. A third exemplary embodiment of the present invention uses the cracking characteristics of newly developed and/or existing types of catalysts to optimize the production of light gas oils, naphtha, and gases from the coking process.

Furthermore, it has been discovered that a catalytic additive can be introduced into traditional coking processes to modify the quantity or yield of a coking process product and/or modify certain characteristics or properties of coking process products. Minor changes in coking process operating conditions can enhance the effectiveness of the catalytic additive package. The change in the products of the coking process is dependent on (but not limited to) (1) the quality and quantity of the catalytic additive package, (2) the existing design and operating conditions of the particular coking process, (3) the types and degree of changes in the coking process operating conditions, and (4) the coking process feed characteristics.

DRAWINGS

FIG. 1 shows an example of the present invention in its simplest form. This basic process flow diagram shows a heated, mixing tank (an exemplary means of mixing and temperature regulation) where components of the present invention's additive can be blended: catalyst(s), seeding agent(s), excess reactant(s), carrier fluid(s), and/or quenching agent(s). The mixed additive is then added to a generic coking process via a properly sized pump (an exemplary means of pressurized injection) and piping, preferably with a properly sized atomizing injection nozzle.

Figure 2:
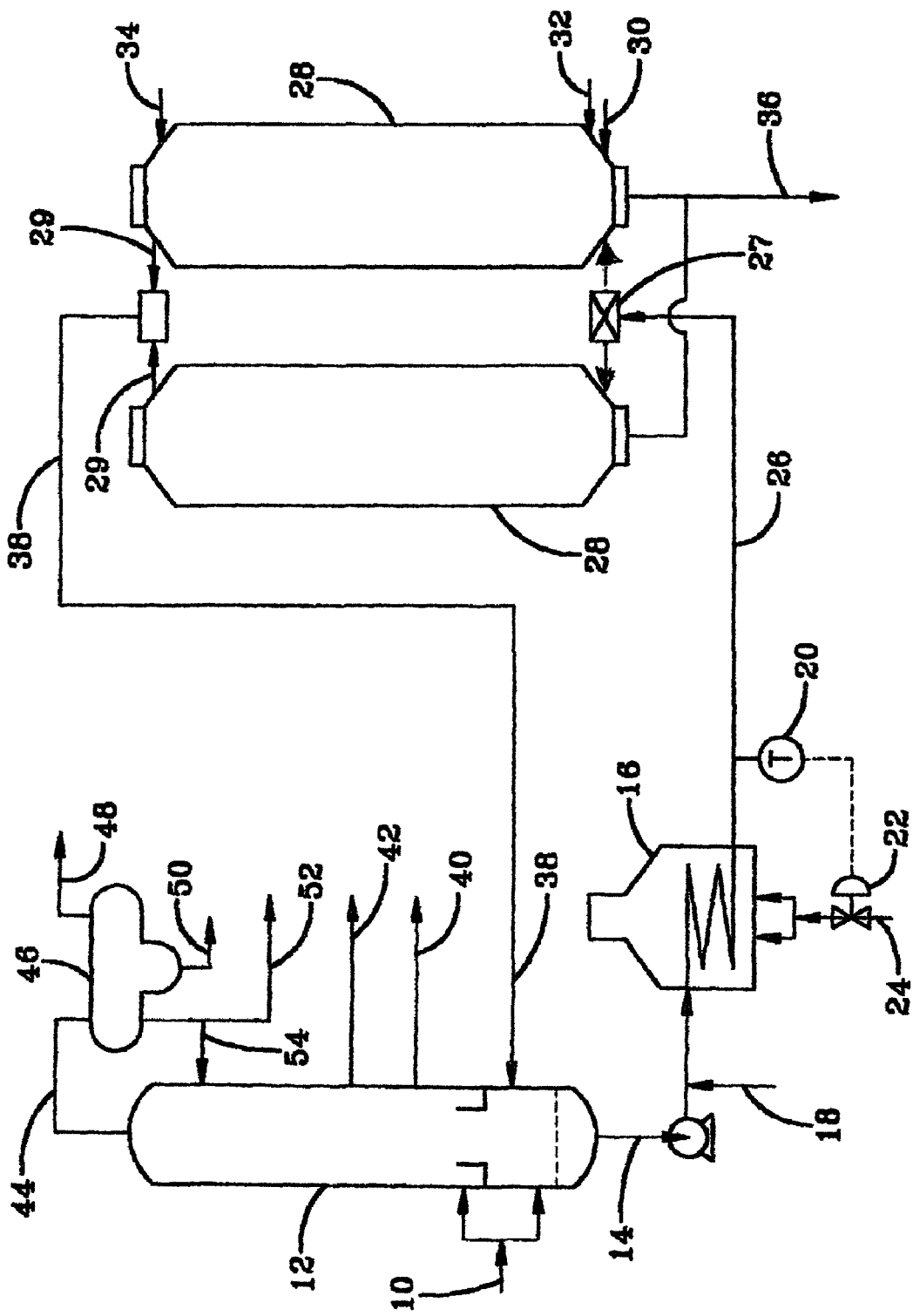

FIG. 2 shows a basic process flow diagram of the traditional, delayed coking technology of the known art.

Figure 3:
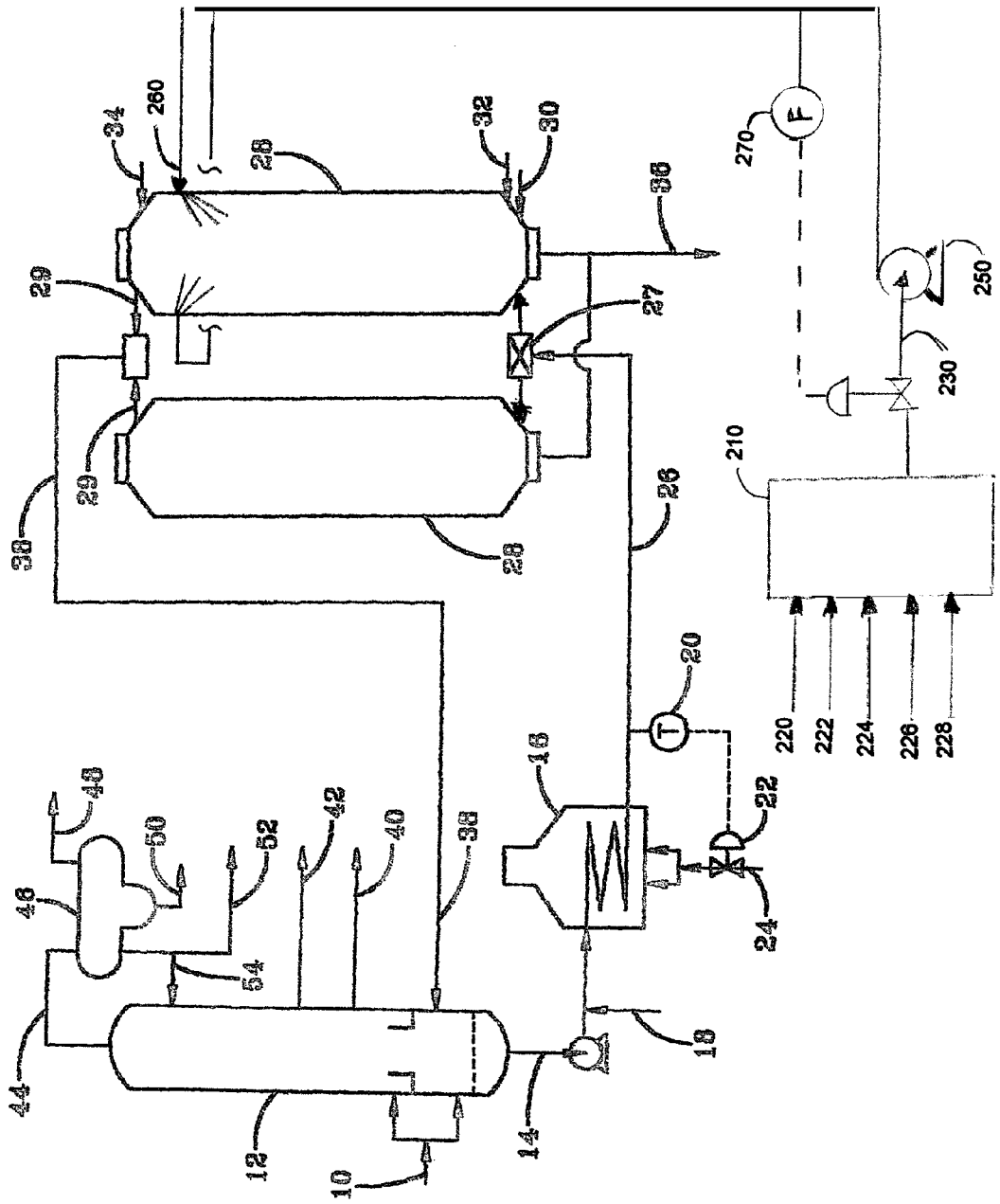

FIG. 3 shows the integration of an example of an additive injection system of the present invention into the delayed coking process. The actual additive injection system may vary from refinery to refinery, particularly in retrofit applications. The injection points can be through injection nozzles at one or more points on the side walls above the vapor/liquid interface (also above the coking interface) in the coking vessel. Alternatively, the injection of the additive can take place at various places: any point above the vapor/liquid interface of the coking vessel, a coking process feed, a coking process recycle, a coking process heater feed, a coking process heater outlet stream, a coking vessel inlet stream, a coking vessel vapor line, a coking process fractionator, or any combination thereof. For example, lances from the top of the coke drum or even a coke stem may move ahead of the rising vapor/liquid interface (e.g. coking mass). Also, the additive injection system may be integrated as part of the existing anti-foam system (i.e. modified anti-foam system to increase flow rates), take the place of the anti-foam system, or be a totally independent system.

Figure 4:
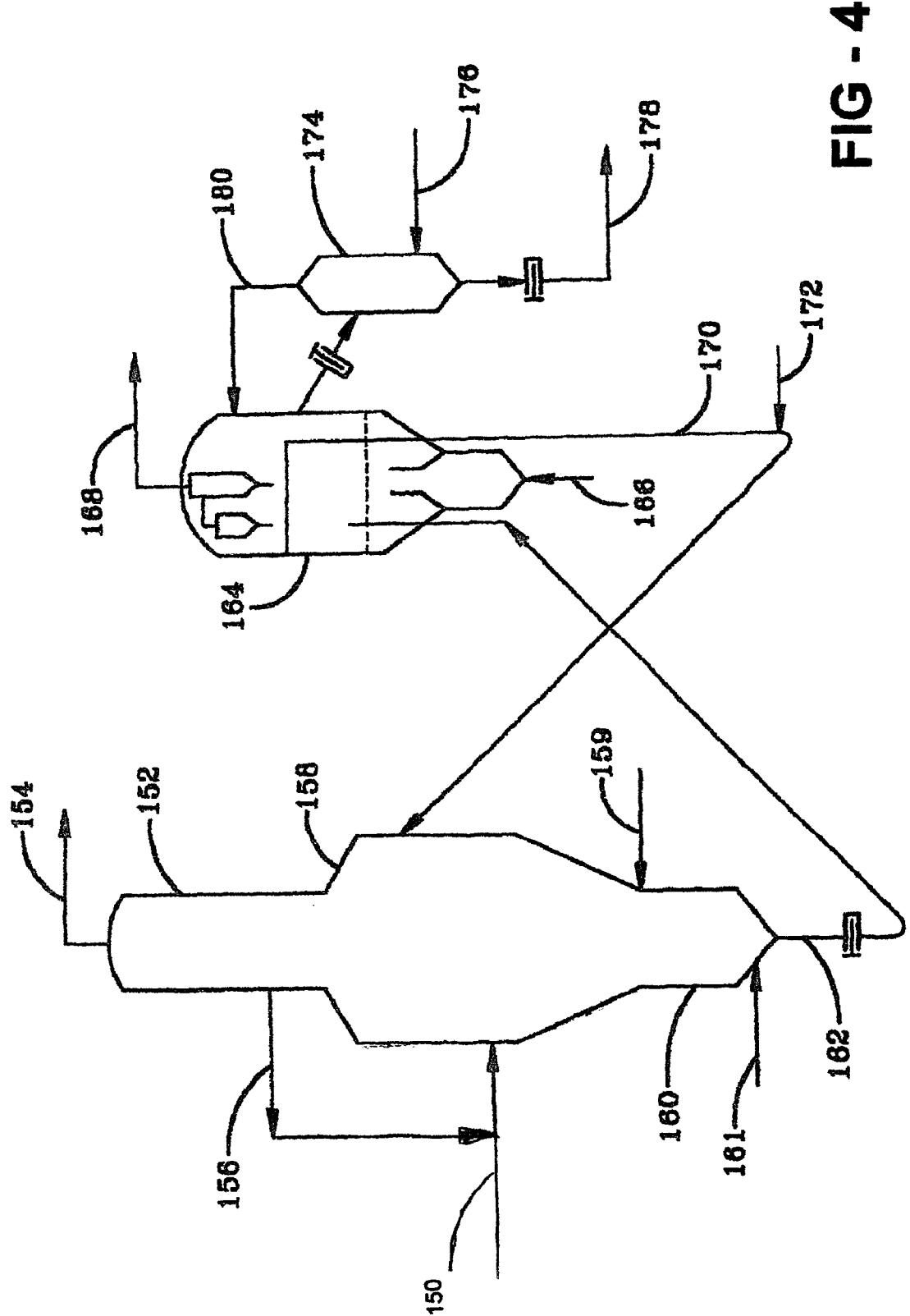

FIG. 4 shows a basic process flow diagram of the traditional, fluid coking technology of the known art. Flexicoking is essentially the same process with an additional gasifier vessel for the gasification of the by-product pet coke.

Figure 5:
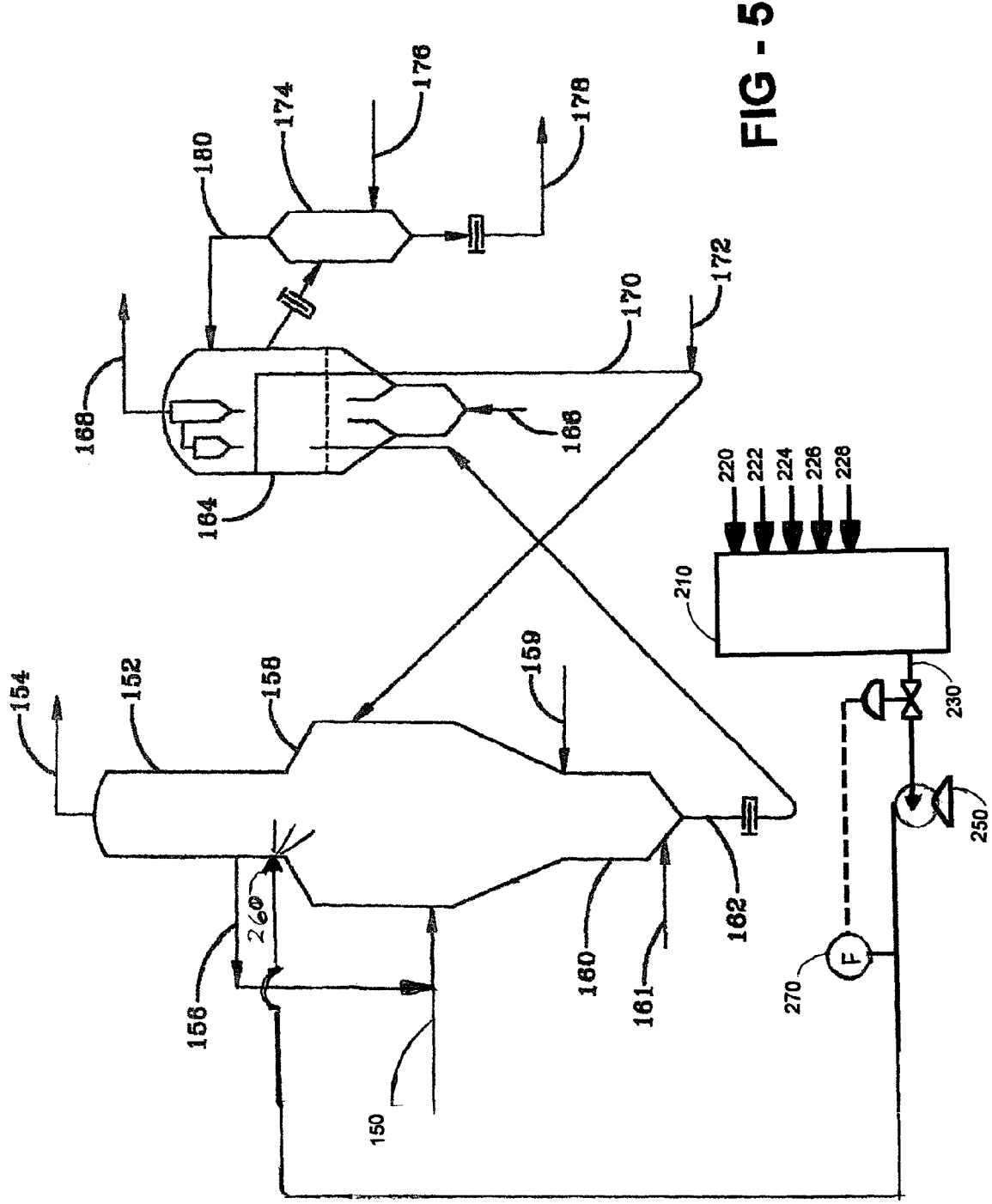

FIG. 5 shows the integration of an example of an additive injection system of the present invention into the fluid coking and flexicoking processes. Similar to the additive system for the delayed coking process, the additive can be injected into the coking vessel above the level where the product vapors separate from the liquid and coke particles (i.e. coking interface in this case) or other injection points (i.e. said various points in a coking process) which may include (but should not be limited to) the fluid coking process feed, the fluid coking process heavy oil recycle to feed, the fluid coking process recycle of carbon particles, the fluid coking process heater feed, a coking process heater outlet stream, the fluid coking process coking vessel inlet stream, the coking vessel vapor line, the coking process fractionator, or any combination thereof. Again, the actual additive injection system may vary from refinery to refinery, particularly in retrofit applications.

DETAILED DESCRIPTION OF THE EXEMPLARY EMBODIMENT(S)

In view of the foregoing summary, the following presents a detailed description of the present invention and its exemplary embodiments, currently considered the best mode of practicing the present invention. The detailed description of the invention provides a discussion of the invention relative to the drawings. The detailed descriptions and discussion of the exemplary embodiments is divided into two major subjects: General Exemplary Embodiment and Other Embodiments. These embodiments discuss and demonstrate the ability to modify (1) the quality or quantity of the catalytic additive package and/or (2) change the coking process operating conditions to optimize the use of an exemplary embodiment of the present invention to achieve the best results in various coking process applications.

Description and Operation of the Invention

General Exemplary Embodiment

Description of Drawings: FIG. 1 provides a visual description of the present invention in its simplest form. This basic process flow diagram shows a heated, mixing tank (210) (as an exemplary means of mixing and means of controlling temperature) where components of the present invention's additive can be blended: catalyst(s) (220), seeding agent(s) (222), excess reactant(s) (224), carrier fluid(s) (226), and/or quenching agent(s) (228). Obviously, if the additive package is comprised of only one or two of these components, the need for a heated, mixing tank or other means of mixing and temperature control can be reduced or eliminated. The mixed additive (230) is then injected into a generic coking process (240) via properly sized pump(s) (250) (as an exemplary means of pressurized injection) and piping, preferably with properly sized atomizing injection nozzle(s) (260). In this case, the pump is controlled by a flow meter (270) with a feedback control system relative to the specified set point for additive flow rate. The primary purpose of this process is to consistently achieve the desired additive mixture of components of the present invention and evenly distribute this additive to introduce said catalyst additive at the desired point or points in the coking process. In general, the system should be designed to (1) handle the process requirements at the point(s) of injection and (2) prevent entrainment of the additive's heavier components (e.g. catalyst) into downstream equipment.

As noted in the invention summary, the specific design of this system and the optimal blend of additive components will vary among refineries due to various factors. The optimal blend can be determined in pilot plant studies or commercial demonstrations of this invention. Once this is determined, one skilled in the art can design this system to reliably control the quality and quantity of the additive components to provide a consistent blend of the desired mixture. This can be done on a batch or a continuous basis. One skilled in the art can also design and develop operating procedures for the proper piping, injection nozzles, and pumping system, based on various site specific factors, including (but not limited to) (1) the characteristics of the additive mixture (e.g. viscosity, slurry particle size, etc.), (2) the requirements of the additive injection (e.g. pressure, temperature, etc.) and (3) facility equipment requirements in their commercial implementation (e.g. reliability, safety, etc.).

Description of Additive: The additive of the present invention maybe a combination of components that have specific functions in achieving the utility of the respective exemplary embodiment. As such, the additive is not just a catalyst in all applications of the present invention, though it can be in many of them. In some applications (e.g. quenching vapor overcracking), there may be no catalyst at all in the additive. Thus, the term 'catalytic additive' does not apply in all cases, but could in many cases. The following discussion provides further breadth of the possible additive components, their utility, and potential combinations.

Said catalytic additive package consists of (1) catalyst(s), (2) seeding agent(s), (3) excess reactant(s), (4) quenching agent(s), (5) carrier fluid(s), or (6) any combination thereof. The optimal design of said catalytic additive package can vary considerably from refinery to refinery due to differences including, but not limited to, coking process feed blend characteristics, process design & operating conditions, coker operating problems, refinery process scheme & processing objectives, downstream processing of the heavy coker gas oil and other coking process products, and/or the pet coke market & specifications.

Catalyst(s): In general, the catalyst consists of any chemical element(s) or chemical compound(s) that reduce the energy of activation for the desired reaction for coker feed, intermediate chemical species of the coking process, and/or other process streams of the coking process. The catalyst can be designed to preferably favor certain cracking reactions and/or provide selectivity for the cracking of specific types of hydrocarbon reactants or products in the coking process (e.g. feed, intermediate and/or vapor products). Furthermore, the catalyst may be designed to preferably favor certain coking reactions and/or provide selectivity for the coking of specific types of hydrocarbon reactants or products, including specifications for coke morphology, quality & quantity of volatile combustible materials (VCMs), concentrations of contaminants (e.g. sulfur, nitrogen, and metals), or combinations thereof. Alternatively, the catalyst may be designed to selectively convert any heavy components (i.e. liquid, semi-liquid, or solid) of the coking process feed that tend to cause "hot spots" in the coke and 'blowouts' in decoking operations. In addition, the catalyst may be designed to preferentially coke via an exothermic, asphaltene polymerization reaction mechanism (vs. endothermic, free-radical coking mechanism). In this manner, the temperature of coke drum can increase, and potentially increase the level of thermal and/or catalytic cracking or coking. These various types of catalyst designs and/or others may be used separately or in any combination thereof. Finally, the catalyst may be formulated to enhance any one or more types of chemical reactions including but not limited to, cracking reactions, coking reactions, pyrolysis reactions, hydrogenation reactions, hydrogenolysis reactions, hydrolysis reactions, addition reactions, dehydrogenation reactions, condensation reactions, polymerization reactions, aromatization reactions, oligomerization reactions, isomerization reactions, or any combination thereof. These reactions may occur in the vapor phase, liquid phase, and/or solid phase.

The foregoing discussion and the general description of catalyst characteristics throughout the description of this invention speak to the breadth of the current invention. Exemplary embodiments of the current invention describe a variety of methods to introduce a variety of catalytic additives (either alone or in combination) into a coking process to enhance a variety of chemical reactions. As such, the current invention anticipates the potential use of wide variety of catalysts, including various catalyst substrates and treatments. In this regard, exemplary embodiments of the catalyst of this invention may include chemical compounds that are not traditional catalysts, yet provide sufficient catalytic effects whether solid, liquid, or gaseous in nature. For example, the presence of certain sodium and calcium compounds can increase undesirable coking in coking process heaters. As such, similar sodium or calcium compounds (e.g. liquid) may be used in an exemplary embodiment of the current invention to enhance coking reactions near the point of injection of a catalytic additive with these compounds. In addition, the development of various catalysts, totally new or based on existing catalysts, is anticipated for exemplary embodiments of the current invention.

Though many types of catalyst can be used to address the catalytic and physical characteristics of the catalyst in exemplary embodiments of the present invention, traditional catalysts that are used for fluid catalytic cracking (FCC) processes of the oil refining industry are believed to be the type of catalyst that presently comes closest to satisfying the desired catalyst characteristics. The primary reasons are (1) high catalytic activity and selectivity for hydrocarbons in a similar operating environment with low pressure and low hydrogen concentration (and thus low hydrogen partial pressure), (2) similar catalyst size requirements, and/or (3) the ability to design and build the most cost effective catalyst to achieve the desired reactions in the various exemplary applications of the current invention. That is, a variety of combinations of basic components of an FCC catalyst may allow a broad range of capabilities, including but not limited to (1) high cracking activity for cracking a variety of hydrocarbons in the coking process (2) high coking activity for exemplary embodiments of this invention for improving coke quality, and/or (3) the optimal combination of various catalyst components and treatments for other applications. The basic components and associated treatments of FCC catalysts include, but are not limited to (1) zeolite synthesis and processing, (2) active matrix synthesis, (3) clay processing, and (4) binder synthesis. The zeolite component is a synthetic (man-made) crystalline aluminosilicate. Various treatments can be used to change the standard Y zeolite to optimize this catalyst component for various objectives, including greater cracking capabilities to desirable products, such as olefins. The second basic component is an active matrix; typically a synthetic amorphous aluminosilicate. This catalyst component is very porous and has a higher concentration of mesopores (30 to 500 angstroms) and macropores (>500 angstroms). This basic catalyst component has higher accessibility for larger molecules in the coking process and has greater bottoms cracking capability. Certain types of clay are used as sinks for heat and sodium, and provides mechanical strength of the catalyst, but have limited effects on catalytic activity. Finally, the binder holds the catalyst components together. Some binders (e.g. alumina polymers) can further increase catalyst activity and aid in bottoms cracking. As such, the key to providing the optimal catalyst for various exemplary embodiments of the current invention in various coking process applications can be finding the right combination of catalyst components and treatments. In this regard, the optimal ratio of zeolite to active matrix (i.e. Z/M in the art) is a primary factor. In conclusion, physical and catalytic characteristics of this type of catalyst may be designed to perform the desired functions of the catalyst in the catalytic additive, described throughout the description of this invention. However, the present invention should not be limited to this type of catalyst due to the many catalyst alternatives, now and in the future. In addition, both the injection of this type of said catalytic additive package and the selective cracking and coking of various feed components, intermediate chemical species, cracked liquids, and/or vapor products are contrary to conventional wisdom and current trends in petroleum coking processes.

Characteristics of exemplary embodiments of catalysts of this invention include a catalyst substrate with activation and treatments to perform the functions stated throughout the description of the current invention. In many (but not all) cases, the catalyst will have acid catalyst sites (e.g. Bronsted and/or Lewis) that initiate the propagation of positively charged organic species called carbocations (e.g. carbonium and carbenium ions), which participate as intermediates in cracking, coking, and other reaction mechanisms. Since many of these reactions are initiated by the propagation of these carboncations, catalyst substrates that promote a large concentration of acid sites are generally preferred, but not required. However, concentrations of acid sites can be too high for the desired reactions (e.g. excessive hydrogen transfer activity). For example, several types of treatments and selection of catalyst components in FCC catalysts, preferably reduce Si/Al ratios to reduce the concentration of acid sites for desired reactions (e.g. production of olefins vs. parafins). For other types of desired catalytic reactions, catalyst substrates of a different nature may be preferred, including non-acid catalyst sites. Alternatively, a catalyst may be in liquid or gaseous form.

Also, the porosity characteristics of solid catalysts of the current invention would need to be designed for the desired reactions in the coking process. In general, the larger the molecular size of the reactants or products, the greater pore size required to mitigate diffusion resistance becoming a limiting factor in the reaction kinetics. For example, asphaltene molecules with molecular weights of 3000 to 48,000 can have molecular diameters of 50 to 300 Angstroms. Acceptable diffusion levels require at least 3 times the molecular diameter: 150 to 900 Angstroms, which is in the upper end of the mesopores range (i.e. 20 to 500 Angstroms) and the lower end of the macro pore range (i.e. >500 Angstroms). Thus, catalysts for these large molecules may preferably have a range of pore size distributions, including the need for a high matrix activity with a distribution of macropores with lower activity to control coke and gas make, and/or mesopores with higher activity. In contrast, traditional FCCU catalysts with an average diameter of 70 microns can have substantial proportions of micropores (zeolites component) with very high activity for predominantly lower boiling point feedstocks with lower molecular size. With a larger proportion of mesopores and macropore characteristics, the catalyst would preferably allow the large, aromatic molecules easy access to the acid sites. In contrast, zeolites have very high acidic activity, but have pore size of approximately 9 angstroms, which are inaccessible to large hydrocarbon molecules. Thus, large hydrocarbon molecules are limited to cracking on the exterior of the zeolite and in the silica-alumina matrix. In addition, the greater the degree of mesoporosity and macroporosity of the catalyst, the longer residence time for reactions to occur at active sites in or near the foam layer, in the liquid layer, and/or in coke layers of the delayed coking process. That is, the probability of continued catalytic reactions after becoming part of the liquid or coke layers is increased with greater catalyst porosity.

In addition, the exemplary embodiments of solid catalysts in the current invention is preferably sized between 10 and 600 microns, (most preferably between 40 and 300 microns) small enough for catalyst fluidization and prevention of injector pluggage, but sufficiently large (e.g. >50 microns) to avoid entrainment in the vapors exiting the coking vessel (e.g. coke drum of the delayed coking process). For example, the catalyst and reactants (e.g. heavy aromatics) would preferably have sufficient density to settle to the vapor/liquid interface (or foam layer), liquid layer, and/or coke layer of a delayed coking process. In this manner, the settling time to the vapor/liquid interface can provide valuable residence time in cracking the various feed components or cracked liquids vapor products (e.g. gas oils) of the coking process, prior to reaching the vapor/liquid interface. For certain heavy aromatics, equilibrium favors maximum aromatics cracking at low temperatures (e.g. 600 to 900 degrees Fahrenheit) preferably 700 to 850 degrees Fahrenheit with long residence times. Conceivably, the catalyst can continue promoting catalytic cracking reactions of the liquids/vapors flowing through the coke, even after it becomes part of the porous coke. If the catalyst and the coke have sufficient porosity, the residence time for cracking potential hydrocarbon reactants (e.g. including a two phase feed flowing through the coke in a coke drum) can conceivably be up to the coker cycle time (e.g. 12 to 15 hours). In contrast, the effective residence time of catalytic reactions of the downstream cracking units (e.g. FCCU) is typically in seconds (e.g. <100 seconds). Potentially, this is believed to be why the heavy aromatics have a greater chance of cracking in the coking process with the catalytic additive of the present invention versus downstream catalytic cracking units (e.g. FCCUs). In this exemplary embodiment of the current invention the catalyst may be preferably be designed to be effective with liquid phase reactants, vapor phase reactants, and/or both. However, the present invention should not be limited to this theory of operation due to the many simultaneous, competing reactions in the coking process. In addition, both the injection of this type of said catalytic additive package and the selective cracking and coking of various feed components, intermediate chemical species, cracked liquids, and/or vapor products are contrary to conventional wisdom and current trends in the petroleum coking processes.

Sizing a solid catalyst of the current invention to promote fluidization (e.g. 40 to >100 microns) for the catalyst in the coking vessel can further enhance the residence time of the catalyst in the vapor zone. However, depending on the catalyst activity, this may not be desirable in many coking processes due to excessive gas production from cracking valuable cracked liquid products to gas. If the catalyst is sized for fluidization, cyclones similar to those in a fluid catalytic cracker (i.e. FCC) or other particle separation equipment could be used in the coking vessel (e.g. coke drum) to control entrainment of catalyst particles in the gas vapors to the fractionation tower, and keep catalyst particles and silica out of the product vapors and fractionator. An exemplary embodiment would include a solid catalyst in the catalytic additive for the fluid coking or flexicoking coking processes, where coke particles up to 600 microns remain fluidized in the coking vessel.

Many types of catalysts can be used for the exemplary embodiments of the present invention. Catalyst substrates can be composed of various porous, natural or man-made materials, including (but should not be limited to) alumina, silica, zeolite, active matrix, activated carbon, crushed coke, calcium compounds, iron compounds, or any combinations thereof. These substrates can be treated or processed to achieve the desired catalytic and physical properties for exemplary embodiments of the current invention. These substrates can also be impregnated or activated with other chemical elements or compounds that enhance catalyst activity, selectivity, other catalyst properties, or combinations thereof. These chemical elements or compounds may include (but should not be limited to) nickel, iron, vanadium, iron sulfide, nickel sulfide, cobalt, calcium, magnesium, molybdenum, sodium, associated compounds, or combinations thereof. For selective cracking, many of the technology advances for selectively reducing coking can be used. For selective coking, the catalyst may likely include nickel, since nickel strongly enhances coking in the absence of significant hydrogen partial pressures. Furthermore, increased levels of porosity, particularly mesoporosity, can be beneficial in allowing better access by larger molecules to the active sites of the catalyst. Though the catalyst in the additive can improve cracking of the coking process feed components and cracked liquids/product vapors (e.g. gas oils) to lighter liquid products, the catalyst normally ends up in the coke. It is anticipated that various catalysts will be designed for the purposes above, particularly catalysts to achieve greater cracking of components of the feed, cracked liquids, and/or product vapors of the coking process to more valuable products. In these cases, a preferred catalyst formulation would initially crack feed components to maximize valuable, lighter products (e.g. cracked liquids), but ultimately promote the cracking or coking of other heavy aromatics to alleviate pitch materials (with a very high propensity to coke vs. crack) in the coke that cause 'hot spots.' However, with certain chemical characteristics of these materials and properly designed catalysts, substantial catalytic conversion of these materials to cracked liquids could be accomplished (e.g. >50 Wt. %).

The optimal catalyst or catalyst combinations for each application of exemplary embodiments of the current invention will often be determined by various factors, including (but not limited to) catalyst cost, catalyst activity, catalyst selectivity for desired reactions, catalyst size, and required pet coke specifications (e.g. metals). In an exemplary embodiment of the current invention, catalysts can be selected from a group consisting of new catalyst, FCCU equilibrium catalyst, spent catalyst, regenerated catalyst, multifunctional catalysts, bimodal catalysts, pulverized catalyst, classified catalyst, impregnated catalyst, treated catalyst, or any combination thereof. For example, coke specifications for fuel grade coke typically have few restrictions on metals, but low cost can be the key issue. In these applications, spent or regenerated FCCU catalysts or spent, pulverized, and classified hydrocracker catalysts (sized to prevent entrainment) may be preferred. However, new, low cost catalysts designed for these purposes or new catalyst enhancers that can be mixed with spent or regenerated catalysts may be most preferred. On the other hand, coke specifications for anode grade coke often have strict limits for sulfur and certain metals, such as iron, silicon, and vanadium. In these applications, cost is not as critical. Thus, new catalysts (preferably made with alumina or activated carbon to prevent metals contamination) designed for high catalyst activity and/or selectivity can be preferred in these applications. Alumina or activated carbon (or crushed coke) impregnated with nickel may be most preferred for applications, where selective coking is desirable.

The amount of catalyst used will vary for each application, depending on various factors, including (1) the catalyst's characteristics (e.g. activity, selectivity conversion, efficiency, and porosity), (2) coke specifications and (3) catalyst cost. In many applications, the quantity of catalyst will be less than 15 weight percent of the coker feed. Most preferably, the quantity of catalyst would be between 0.1 weight percent of the coker feed input to 7.0 weight percent of the coker feed input. Above these levels, the costs will tend to increase significantly, with diminishing benefits per weight of catalyst added. In some cases, the catalytic additive may not include a traditional catalyst at all, but still have desired effect(s) of the catalytic additive package. As described, the catalytic additive(s) can be added at various points in a coking process, including but not limited to an injection into the vapors exiting the coking vessel (e.g. above the vapor/liquid interface or foam layer in the coke drum during the coking cycle of the delayed coking process) by various means, including pressurized injection with or without carrier fluid(s): hydrocarbon(s), oil(s), inorganic liquids, water, steam, nitrogen, or combinations thereof. The means of pressurizing the catalytic additive include (but should not be limited to) a pump or compressed fluids as part of the catalytic additive or separately as a driving force only (e.g. compressed fluid in mixing tank to push through lines and through 'injector') the compressed fluid may include (but should not be limited to) nitrogen, hydrogen, fuel gas, water, hydrocarbon liquid/vapor, air, and/or oxygen. Air and/or oxygen would be the least desirable driving fluid due to potential injection into coking process, causing dangerous fire or explosion potential. 'Injectors' will refer to various devices to conduct the catalytic additive to the injection point for the introduction of said catalytic additive into the coking process of exemplary embodiments of the current invention. Acceptable 'injectors' would include (but should not be limited to) fluid atomizers, nitrogen assist atomizers, atomization systems, injector systems, lances, and/or simply pipe. For example, an injector system may be as sophisticated as a modified drill stem that is retracted through the upper drum flange to keep catalytic additive injection above the rising coke mass above the foam layer. Other injection points (i.e. said various points in a coking process) to add the catalytic additive may include (but not limited to) a coking process feed line, a coking process vapor line, a coking process fractionator, a coking process feed pump, a coking process heater, or any combination thereof. Other process streams where the catalytic additive can be injected into include (but should not be limited to). a coking process feed, a coking process recycle, a coking process heater feed, a coking process heater outlet stream, a coking vessel inlet stream, a coking vessel vapors, a coking process fractionator bottoms, or any combination thereof.

In some exemplary embodiments of the current invention, addition of catalyst alone can be undesirable. That is, injection of a catalyst without excess reactant(s), quenching agent(s), and/or carrier oil, can actually increase undesirable reactions (e.g. vapor overcracking) and cause negative economic impacts.

Seeding Agent(s): In general, the seeding agent consists of any chemical element(s) or chemical compound(s) that enhances catalytic cracking or catalytic coking, particularly the formation of coke by providing a surface for the coking reactions and/or the development of coke crystalline structure (e.g. coke morphology) to take place. The seeding agent can be a liquid droplet, a semi-solid, solid particle, or a combination thereof. The seeding agent can be the catalyst itself or a separate entity. Compounds of sodium, calcium, iron, and carbon particles (e.g. crushed coke or activated carbon) are known seeding agents for coke development in refinery processes. These and other chemical elements or compounds can be included in the catalytic additive to enhance cracking or coke development from feed components or chemical intermediates in the coking process.

The amount of seeding agent(s) used will vary for each application, depending on various factors, including (but not limited to) the amount of catalyst, catalyst characteristics (e.g. activity, selectivity conversion, efficiency, and porosity), coke specifications, and cost. In many applications, catalytic cracking will be more desirable than catalytic coking. In these cases, seeding agents that enhance catalytic coking may be minimized or not included at all, and the catalyst will be the only seeding agent. However, in some cases, little or no catalyst may be desirable in the additive. In such cases, the amount of seeding agent will be less than 15 weight percent of the coker feed. Most preferably, the quantity of seeding agent would be between 0.1 weight percent of the coker feed input to 7.0 weight percent of the coker feed input. In many cases, the amount of seeding agent is preferably less than 3.0 weight percent of the coker feed. As described, this seeding agent can be added to various points in the coking process by various means, including (but not limited to) pressurized injection with or without carrier fluid(s): hydrocarbon(s), oil(s), inorganic liquids, water, steam, nitrogen, or combinations thereof.

Excess Reactant(s): In general, the excess reactant consists of any chemical element(s) or chemical compound(s) that react with feed components, intermediate chemical species, and/or product vapors of the coking process to provide the desired reactions and reaction products. In the catalytic additive, the excess reactant can be a gas, a liquid, a semi-solid, solid particle or a combination thereof. Preferably, the excess reactants of choice are chemically reactive compounds.

Various types of excess reactants can be used for this purpose. Ideally, the excess reactant would contain very high concentrations of chemical elements or chemical compounds that react directly with a desired feed component, intermediate chemical species, cracked liquids, and/or vapor products of the coking process in the vapor phase, liquid phase, solid phase, or any combination thereof. Excess reactants would include, but should not be limited to, slurry oils, gas oils, extract from aromatic extraction units (e.g. phenol extraction unit in lube oil refineries), coker feed, bitumen, other aromatic oils, crushed coke, activated carbon, or combinations thereof. These excess reactants can be further processed (e.g. distillation) to increase the concentration of desired excess reactants components (e.g. aromatic compounds) and reduce the amount of excess reactant required and/or improve the reactivity, selectivity, or effectiveness of excess reactants with the targeted feed component(s), intermediate chemical species, cracked liquids, and/or product vapors of the coking process.

In some cases, the injection of hydrogen or other reactive gas, either with the catalytic additive or separately, may be desirable to enhance the catalyst's effectiveness. This is particularly true for situations where additional yields of cracked liquids would occur from mild hydrotreating, hydrocracking, hydroprocessing, or any combination thereof. An exemplary embodiment of the current invention with hydrogen injection would include high pressure coking vessels, such as needle cokers with pressures in excess of 80 psig.

The amount of excess reactant used will vary for each application, depending on various factors, including (but not limited to) the amount of catalyst, catalyst characteristics (e.g. activity, selectivity conversion, efficiency, and porosity), coke specifications, and cost. In many applications, the quantity of excess reactant will be sufficient to provide more than enough moles of reactant to achieve the desired conversion of feed components, intermediate chemical species, cracked liquids, and/or vapor products in a coking process. Preferably, the molar ratio of excess reactant to targeted component(s) of the coking process would be in excess of that determined by one skilled in the art. However, in some cases, little or no excess reactant can be desirable in the additive. In many cases, the amount of excess reactant will be less than 15 weight percent of the coker feed. Most preferably, the quantity of excess reactant would be between 0.1 weight percent of the coker feed input to 7.0 weight percent of the coking process feed input. As described, this excess reactant can be added to various points in the coking process by various means, including (but not limited to) pressurized injection with or without carrier fluid(s): gas oils hydrocarbon(s), oil(s), inorganic liquids, water, steam, nitrogen, or combinations thereof.

Carrier Fluid(s): In general, a carrier fluid consists of any fluid that makes the catalytic additive easier to inject into the coking process. The carrier can be a liquid, gas, hydrocarbon vapor, or any combination thereof. In many cases, the carrier will be a fluid available at the coking process, such as gas oils or lighter liquid process streams, such as kerosene. In many cases, gas oil at the coking process is the preferable carrier fluid. However, carriers would include, but should not be limited to, FCCU slurry oils, decanted FCCU slurry oils, FCCU cycle oils, gas oils, other hydrocarbon(s), other oil(s), inorganic liquids, water, steam, nitrogen, hydrogen, or combinations thereof.

The amount of carrier fluid(s) used will vary for each application, depending on various factors, including (but not limited to) the amount of catalyst, characteristics (e.g. activity, selectivity conversion, efficiency, and porosity), coke specifications, and cost. In many applications, little or no carrier is actually required, but desirable to make it more practical or cost effective to add the catalyst additive into the coking process. The quantity of carrier fluid(s) will be sufficient to improve the ability to pressurize the additive for addition via pump or otherwise. In many cases, the amount of carrier will be less than 15 weight percent of the coker feed. Most preferably, the quantity of carrier fluid(s) would be between 0.1 weight percent of the coker feed input to 7.0 weight percent of the coker feed input. As described, this carrier fluid can help with addition of the catalytic additive into various points of the coking process by various means, including (but not limited to) pressurized injection.

Quenching Agent(s): In general, a quenching agent consists of any fluid that has a net effect of further reducing the temperature of various points in a coking process. The quenching agent(s) can be a liquid, gas, hydrocarbon vapor, or any combination thereof. Many refinery coking processes use a quench in the vapors downstream of the coking vessel (e.g. coke drum). In some cases, this quench can be moved forward into the coking vessel. In many cases, a commensurate reduction of the downstream quench can be desirable to maintain the same overall heat balance in the coking process. In many cases, gas oil available at the coking process will be the preferred quench agent. However, quenching agents would include, but should not be limited to, gas oils, FCCU slurry oils, FCCU cycle oils, other hydrocarbon(s), other oil(s), inorganic liquids, water, steam, nitrogen, or combinations thereof. The quenching agent(s) may be added either with the additive and/or separately, may be desirable to enhance the catalyst's effectiveness.

The amount of quench used will vary for each application, depending on various factors, including (but not limited to) the temperature of the coking process, the desired temperature of the coking process, and the quenching effect of the additive without quench, and/or characteristics and costs of available quench options. In many applications, the quantity of quench will be sufficient to finish quenching the vapors from the primary cracking and coking zone(s) in a coking vessel to the desired temperature. In some cases, little or no quench can be desirable in the additive. In many cases, the amount of quench will be less than 15 weight percent of the coker feed. Most preferably, the quantity of quench would be between 0.1 weight percent of the coker feed input to 7.0 weight percent of the coker feed input. As described, this quench can be added to various points in a coking process as part of the additive by various means, including (but not limited to) pressurized injection with or without carrier fluid(s): gas oils hydrocarbon(s), oil(s), inorganic liquids, water, steam, nitrogen, or combinations thereof.

Additive Combination and Injection: The catalytic additive components can be added to the coking process in combination or separately. In many applications, a blended additive would combine any or all of the 5 components to the degree determined to be desirable in each application. The catalytic additive components would be blended by a means of mixing, preferably to a homogeneous consistency, and heated to the desired temperature (e.g. heated, mixing tank) by a means of temperature regulation. For example, the desired temperature (e.g. >150 degrees F.) of the mixture may need to be increased to maintain a level of viscosity for proper pumping characteristics and fluid nozzle atomization characteristics. The additive, at the desired temperature and pressure, would then be pressurized (e.g. via pump) and added (e.g. via injection nozzle) to a coking process at the desired point. In many cases, insulated piping will be desirable to keep the additive at the desired temperature. Also, injection nozzles can be desirable in many cases to evenly distribute the additive across the cross sectional profile of the coking process (e.g. coking vessel). The injection nozzles would also be designed to provide the proper droplet size (e.g. 50 to 600 microns) to prevent entrainment of undesirable components into other components of the coking process. Typically, these injection nozzles would be aimed countercurrent to the flow of coking process. The injection velocity should be sufficient to penetrate the process flow and avoid undesirable entrainment into the coking process streams. However, the injection nozzles design and metallurgy must take into account the potential for plugging and erosion from the solids (e.g. catalyst) in the catalytic additive package, since the sizing of such solids must be sufficient to avoid entrainment into undesirable components of the coking process (e.g. product vapor stream). As described, the catalytic additive(s) can be added at various points in a coking process, including but not limited to an injection into the vapors in the coking vessel (e.g. above the vapor/liquid interface or foam layer in the coke drum during the coking cycle of the delayed coking process) by various means, including pressurized injection with or without carrier fluid(s): hydrocarbon(s), oil(s), inorganic liquids, water, steam, nitrogen, or combinations thereof. The means of pressurizing the catalytic additive include (but should not be limited to) a pump or compressed fluids as part of the catalytic additive or separately as a driving force only (e.g. compressed fluid in mixing tank to push through lines and through 'injector') the compressed fluid may include (but should not be limited to) nitrogen, hydrogen, fuel gas, water, hydrocarbon liquid/vapor, air, and/or oxygen. Air and oxygen would be the least desirable driving fluid due to potential injection into coking process, causing dangerous fire or explosion potential. 'Injectors' refer to various devices to conduct the catalytic additive to the injection point for the introduction of said catalytic additive into the coking process of exemplary embodiments of the current invention. Acceptable 'injectors' would include (but should not be limited to) fluid atomizers, nitrogen assist atomizers, atomization systems, injector systems, lances, and/or simply pipe. For example, an injector system may be as sophisticated as a modified drill stem that is retracted through the upper drum flange to keep catalytic additive injection above the rising coke mass above the foam layer. Other injection points (i.e. said various points in a coking process) to add the catalytic additive may include (but not limited to) a coking process feed line, a coking process vapor line, a coking process fractionator, a coking process feed pump, a coking process heater, or any combination thereof. Other process streams where the catalytic additive can be injected into include (but should not be limited to). a coking process feed, a coking process recycle, a coking process heater feed, a coking process heater outlet stream, a coking vessel inlet stream, a coking vessel vapors, a coking process fractionator bottoms, or any combination thereof.

The catalytic additive package of the current invention may also include anti-foam solution that is used by many refiners to avoid foamovers. These antifoam solutions are high density chemicals that typically contain siloxanes to help break up the foam at the vapor/liquid interface (or foam layer) by its affect on the surface tension of the bubbles. In many cases, the additive package of the current invention may provide some of the same characteristics as the antifoam solution; significantly reducing the need for separate antifoam. In addition, the existing antifoam system may no longer be necessary in the long-term, but can be modified for commercial trials and/or implementation of the current invention. It should be noted that not all coking vessels have a foam layer (depending on feed character and operating conditions). Thus, vapor/liquid interface will be often used, though 'foam layer' is synonymous in most delayed cokers.

Said catalytic additive is believed to catalytically convert any feed components, intermediate chemical species, cracked liquids, or vapor products of the coking process by (1) providing a catalyst to reduce the activation energy of the desired chemical reactions, and/or (2) providing an excess reactant and appropriate reaction conditions to promote the desired chemical reactions in a vapor phase, liquid phase, solid phase, semi-solid phase, or any combination thereof. That is, said catalytic additive with a catalyst that has sufficient activity (e.g. active sites), sufficient selectivity, and sufficient porosity characteristics to reduce diffusion resistance can be used with or without excess reactant(s), quenching agent(s), seeding agent(s), carrier fluid(s), and/or anti-foam agent(s) to achieve the proper conditions for a desired chemical reaction(s) to produce a desired product(s). Said catalyst can be a solid, a liquid, and/or a gas and be homogeneous or heterogeneous in nature. As such said catalyst can react with a reactant(s) of the coking process in the gas phase, liquid phase, solid phase, or any combination thereof. In most cases, (1) the reactants can diffuse to the catalysts' active sites, (2) the reactants react to form the desired products, byproducts, or any combination thereof, and (3) the products and/or byproducts diffuse from the catalyst's active sites. In cases where the catalytic additive is injected into the product vapors in the coking vessel above the coking mass, the localized quench effect of the catalytic additive can cause the highest boiling point components (e.g. heavy aromatics) in the vapors to condense on the catalyst and/or seeding agent, and cause selective exposure of the said highest boiling point components to the catalysts' active sites. In this manner, selective cracking may occur in the liquid phase or in the gaseous phase, after these condensed materials revaporize as they (catalyst, highest boiling point material, and other additive components) settle to the vapor/liquid interface and reheat. After cracking the reactant(s), the cracked liquid products of lower boiling point will vaporize and/or then leave the catalyst active site. This vaporization causes another localized cooling effect that condenses the next highest boiling point component. Conceivably, this process can be repeated until the catalyst active site is blocked, poisoned, or otherwise made ineffective or the coking cycle ends. Equilibrium for some catalytic cracking (vs. coking) reactions (e.g. heavy aromatics) have been shown to favor lower temperatures (e.g. 600 to 875° F. vs. 875 to 925° F.), if given sufficient residence time and optimal catalyst porosity and activity levels. With the injection of the catalytic additive, the temperature of the product vapors in the coking vessel can range from 750 to 875 degrees Fahrenheit. The additive settling time and the time at or below the vapor/liquid interface (i.e. in the foam layer, liquid layer and coke layer) provide much longer residence times than encountered in other catalytic cracking units (e.g. FCCU). Thus, the ability to crack certain hydrocarbons is enhanced by this method of catalytic cracking. Ideally, the additive's active sites in many applications would repetitively crack hydrocarbons, prior to and after reaching the vapor/liquid interface (or foam layer), liquid layer, or coke layer, before cracking and/or coking additional hydrocarbon components and being integrated into the petroleum coke. This invention should not be limited by this theory of operation. However, both the injection of this type of said catalytic additive package and the selective cracking and coking of various feed components, intermediate chemical species, cracked liquids, and/or vapor products are contrary to conventional wisdom and current trends in the petroleum coking processes.

Enhancement of Additive Effectiveness: It has also been discovered that minor changes in coking process operating conditions can enhance the effectiveness of the catalytic additive package. The changes in coker operating conditions include, but should not be limited to, (1) reducing the coking vessel outlet temperature, (2) increasing the coking vessel outlet pressure, (3) reducing the coking feed heater outlet temperature, or (4) any combination thereof. The first two operational changes represent additional means to condense the highest boiling point materials in the product vapors to increase their residence time in the coking vessel. In many cases, the additive package is already lowering the temperature of the product vapors by its quenching effect and the intentional inclusion of a quenching agent in the additive package to increase this quenching effect. This quench effect reduces vapor overcracking reactions, as well as increases condensation of the highest boiling point materials in the product vapors. However, many coking units have a substantial quench of the product vapors in the vapor line between the coking vessel and the fractionator to prevent coking of these lines. In many cases, it may be desirable to move some of this quench upstream into the coking vessel. In some coking units, this can be accomplished by simply changing the direction of a quench spray nozzle (e.g. countercurrent versus co-current). As noted previously, a commensurate reduction in the downstream vapor quenching is often desirable to maintain the same overall heat balance in the coking process unit. If the coking unit is not pressure (compressor) limited, slightly increasing the coking vessel pressure can be preferable in many cases due to less vapor loading (caused by the quenching effect) to the fractionator and its associated problems. Finally, slight reductions of the feed heater outlet temperature may be desirable, in some cases, to optimize the use of the additive in the present invention. In some cases, reduction of the cracking of heavy aromatics and asphaltenes to the 'heavy tail' components of the coking process gas oils can reduce the amount of additive required to remove the 'heavy tail' and improve its effectiveness in changing coke morphology from shot coke to sponge coke crystalline structure. In some cases, other operational changes in the coking process can be desirable to improve the effectiveness of the present invention.

In the practical application of an exemplary embodiment of the present invention, the optimal combination of methods and embodiments will vary significantly. That is, site-specific, design and operational parameters of the particular coking process and refinery must be properly considered. These factors include (but should not be limited to) coker design, coker feedstocks, and effects of other refinery operations. With the present invention, one skilled in the art can readily determine the optimal combination of methods and embodiments presented herein, and apply them accordingly to site-specific, design and operational parameters of the particular coking process and refinery.

Description of Additive Reactants: Exemplary embodiments of the present invention generally introduce a catalytic additive into the coking vessel of the coking process at or above the vapor/liquid interface or, alternatively, at or above the coking interface (i.e. the coke/liquid interface). In this manner, the primary reactants exposed to the catalyst in exemplary embodiments of the present invention are (1) the vapor products resulting from the thermal cracking and thermal coking of the coker feed and (2) essentially coker feed derivatives (also from thermal cracking and thermal coking) in the liquid, emulsion, and foam layers (below the vapor/liquid interface), after the catalyst has settled there. As such, the primary catalytic reactants in exemplary embodiments of the present invention have substantially different chemical and physical characteristics than the reactants of the known art, wherein catalyst is added to the coker feed of the coking process.

The hydrocarbon feed of the coking process is typically a residuum process stream (e.g. vacuum tower bottoms), comprised of very heavy aromatics (e.g. asphaltenes, resins, etc.) that have theoretical boiling points greater than 1050 degrees Fahrenheit. Typical ranges (Wt. %) of SARA for the coker feed components are as follows: 1-10% Saturates, 10-50% Aromatics, 30-60% Resins, and 15-40% Asphaltenes. As such, the primary reactants exposed to the catalysts of the known art are heavy aromatics with a substantially higher propensity to coke, particularly with the exposure to high vanadium and nickel content in the coker feed. Furthermore, mineral matter in the coker feed tends to act as a seeding agent that further promotes coking. Calcium, sodium, and iron compounds/particles in the coker feed have been known to increase coking, particularly in the coker feed heater. Similarly, the catalyst may act as a seeding agent, as well.

From a physical perspective, the primary reactants of the known art (i.e. catalyst in the feed) are a very viscous liquid (some parts semi-solid) at the inlet to the coker feed heater. Throughout the heater and into the coke drums the feed becomes primarily hot liquid, some solids (from feed minerals and coking), and vapors (e.g. from coker feed cracking). The temperature of the multi-phase material at the inlet to the drum is typically between 900 and 950 degrees Fahrenheit.

In contrast, the catalyst reactants in an exemplary embodiment of the present invention are primarily derivatives (or partially cracked portions) of the coker feed. That is, the reactants that are exposed to the catalyst additive in exemplary embodiments of the present invention are mostly the products of the thermal cracking and thermal coking of the coker feed. The catalyst additive of the exemplary embodiments of the present invention have very limited exposure to coking process feed components, when the catalyst settles to the liquids above the coking interface (e.g. coke/liquid interface) and becomes part of the solid coke. Even here, most of the coker feed has been converted to smaller compounds with lower propensity to coke (vs. coking process feed). Thus, reactants exposed to the catalyst additive of the present invention are substantially more likely to crack than the components of the coker feed that are exposed to catalysts introduced into the coking process feed in the known art.

The product vapors at or above the vapor/liquid interface in the coking vessel comprise various derivatives of the coker feed components, that are thermally cracked upstream of this point in the coking vessel. In the known art, these product vapors continue to thermally crack until they exit the coking vessel, where they are typically quenched in the vapor line to stop coking and cracking reactions. After fractionation, these product vapors (many condensed) are normally classified by boiling point range into the following groups: gas (less than 90 degrees Fahrenheit), light naphtha (roughly 90 to 190 degrees Fahrenheit), heavy naphtha (roughly 190 to 330 degrees Fahrenheit), Light Coker Gas Oil—LCGO (roughly 330 to 610 degrees Fahrenheit), Heavy Coker Gas Oil—HCGO (roughly 610 to 800 degrees Fahrenheit), and coker recycle (greater than roughly 800 degrees Fahrenheit). The vapor products in the coking vessel can be thought of as having the same boiling point classifications at any point in time that it is exposed to a catalytic additive of the present invention. However, the vapor products are recognized to have higher proportions of heavier products than what comes from the fractionator due to further thermal cracking in the vapors prior to the vapor line quench and the fractionator. In other words, the further upstream from the fractionator, the higher the proportions of heavier products.

Below the vapor/liquid interface (down to the coking interface and below), the solids, liquids, and vapors comprise mostly chemical compounds of converted coker feed components. As the catalyst in an exemplary embodiment of the present invention settles into the foam and liquid layers, it may be exposed to these solids, liquids and vapors. In many cases, the solid portions represent coke from thermal coking of the coker feed components. The liquid and some semi-solid portions in these layers may contain components of the coker feed, but many of the liquids are likely derivatives (or cracked) components of the coker feed at this point, particularly toward the end of the coking cycle. At this level, the vapors emerging from the coking interface are essentially cracked coker feed components, derivatives of the heavier saturates, aromatics, resins, and asphaltenes in the coking process feed that have theoretical boiling points greater than 1050 degrees Fahrenheit. Conceivably, the catalyst of exemplary embodiments of the present invention can still facilitate cracking and coking reactions, even as the catalyst becomes part of the coke layer. At this level, the catalyst is still exposed primarily to derivatives of the coker feed: coke and vapor/liquids passing through the coke layer. In conclusion, even after settling to the vapor/liquid interface and below, the catalyst in exemplary embodiments of the present invention can still facilitate cracking and coking reactions (inherent aspects of the present invention). Even at these levels, the overall exposure of the catalyst to coker feed components with a higher propensity to coke is limited.

In the known art of the refining industry, the product classifications have broader classification of low boiling point, middle boiling point, and high boiling point materials or products. Typically, the classification of low boiling point products comprises the chemical compounds that are in the gas phase at ambient temperatures and pressures, including methane, ethane, propanes, butanes, and the corresponding olefins. These compounds typically have boiling points less than roughly 90 degrees Fahrenheit, and are commonly referred to C4- in the industry, referring to the number of carbon atoms in each molecule. The middle boiling point products are typically liquids at ambient temperatures and pressures, and boiling points between roughly 90 and 610 degrees Fahrenheit. Most of these middle boiling point products, including middle distillates, are blended into liquid transportation fuels either directly or after further processing (e.g. hydrotreating, reforming, isomerization) to improve product qualities. Typically, high boiling point materials are considered to be refinery process streams with boiling point ranges greater than the middle distillates. These process streams normally require further processing (e.g. hydrocracker or fluid catalytic cracking unit) to lower their boiling point range before they can be blended into liquid transportation fuels. Generally, these materials have boiling points greater than the highest end point of the middle distillates; typically the end point of light gas oils or approximately 610 degrees Fahrenheit.

Applying this known art to a coking process, the coker recycle and Heavy Coker Gas Oil (HCGO) would be classified as 'high boiling point materials' in the product vapors in the coking vessel. As discussed in other parts of this description, some exemplary embodiments of the present invention can use the catalytic additive in to quench the vapor products and condense the 'highest boiling point' materials in the product vapors. By condensing these highest boiling point materials, exemplary embodiments of the present invention can essentially create an 'internal recycle' that increases the residence time of the heaviest components of the coker recycle and/or part of the HCGO. In addition, this 'internal recycle' may also be used to provide intimate contact with the catalyst and make it more selective and efficient, thereby lowering catalyst makeup requirements and costs. However, the catalyst must be designed to crack effectively with these very large molecules in the liquid phase, until the catalyst settles to a level in the coking vessel where these highest boiling point materials revaporize due to the higher temperatures or other local sources of heat (e.g. release of heat from condensation of adjacent molecules). The quantity of 'internal recycle' depends on various factors, including (1) the coking vessel outlet temperature of the known art, (2) the quantity of catalytic additive and its associated quenching effect, and (3) the quality and quantity of coker recycle and Heavy Coker Gas Oil. In exemplary embodiments of the present invention, catalytic cracking of the highest boiling point materials in the product vapors of the coking vessel may allow one skilled in the known art to reduce the quantity of traditional coker recycle (i.e. external) and/or reduce the amount of 'heavy tail' components in the HCGO. Where the reduction shows up can be optimized by adjusting the end point of the HCGO in the fractionator operation.

From a physical perspective, the primary catalytic reactants of the present invention are primarily vapors, condensed liquids of the highest boiling point vapors, and liquids, semi-solids and solids at the coking interface (after the catalyst settles to the vapor/liquid interface and below). The temperature of the primary reactants is typically <875° F., which is normally more conducive to aromatic cracking (vs. coking) with high residence time and reaction equilibrium, favoring these lower temperatures. Physically, the primary catalytic reactants of exemplary embodiments of the present invention are substantially different from the primary catalytic reactants of the known art and much less conducive to coking.

In summary, the chemical and physical characteristics of the catalyst reactants are vastly different for an exemplary embodiment of the present invention, when compared to the chemical characteristics of the catalytic reactants of the known art. That is, the catalyst additive of an exemplary embodiment of the present invention is typically added to the coking vessel downstream of the primary cracking and coking zones of the coking process. In these cases, the primary reactants are derivatives of the coker feed after extensive cracking and coking of the coker feed: coker recycle, heavy coker gas oil (HCGO), light coker gas oil (LCGO), naphtha, and various gases with less than 5 carbon atoms per molecule. The highest boiling point materials (e.g. greater than roughly 800 degrees Fahrenheit) in the coker product vapors are the coker recycle and the 'heavy tail' of the heavy coker gas oil. Consequently, the primary reactants exposed to the catalyst of an exemplary embodiment of the present invention are substantially smaller molecules that are more conducive to cracking (vs. coking) than the known art. Chemically, the primary catalytic reactants of an exemplary embodiment of the present invention are substantially different and much less conducive to coking than the primary catalytic reactants of the known art.

The physical and chemical characteristics of the primary reactants in the present invention are more similar to those in a fluid catalytic cracking unit (FCCU). That is, a typical FCCU further processes the HCGO generated by the coking process. The FCCU is typically used to convert (catalytically crack) the high boiling point materials (e.g. greater than roughly 610 degrees Fahrenheit) of the HCGO in a similar operating environment with low pressure, limited hydrogen, and slightly higher temperatures. However, the substantially longer residence time for the catalyst in exemplary embodiments of the present invention (potentially hours vs. seconds) is advantageous in achieving efficient use of the catalyst with reaction kinetics that may more closely approach equilibrium values.

Differentiation Over Fluid Catalytic Cracking Process: The known art of fluid catalytic cracking in the refining industry is very different from the introduction of a catalytic additive in the coking vessel of a coking process in exemplary embodiments of the present invention. The fluid catalytic cracking (FCC) process typically introduces high boiling point hydrocarbon feed(s) into fluidized catalyst particles in a specially designed reactor (e.g. combinations of feed-riser and dense-bed reactors). The high boiling point feeds typically include heavy atmospheric gas oil, vacuum gas oil, and/or heavy coker gas oil (HCGO). The catalyst sufficiently lowers the activation energy of cracking reactions to preferably promote the catalytic cracking of these high boiling point materials to lower boiling point hydrocarbon products, including gasoline and middle distillates. In addition, FCC catalysts typically increase some coking reactions, as well. Thus, the FCC process also produces coke that remains on the catalyst and rapidly lowers its activity. Consequently, the catalyst is circulated to a regeneration vessel, where the coke is burned off of the catalyst to regenerate catalyst activity to acceptable levels.

The reaction conditions of the FCC reactor are also substantially different from the vapor zone of the coking vessel. The catalytic reactants in both processes typically include heavy coker gas oil, but the vapor products in the coking vessel of the coking process also include higher boiling point compounds in the coker recycle component and lower boiling point compounds in the components of light coker gas oil, naphtha, and gases. Typically, the FCC reactor pressure (e.g. 8-12 psig) is slightly lower than the coking vessel (e.g. 12-25 psig). The FCC reactor temperature (e.g. 900 to 1000 degrees Fahrenheit) is substantially higher than the coking vessel (e.g. 800 to 900 degrees Fahrenheit). Furthermore, the residence time of catalyst exposure to the reactants is substantially different: FCC typically measured in seconds, where the catalyst in the coking vessel can conceivably continue to catalyze reactions for minutes to hours, depending on various factors including fluidization in the coking vessel product vapors. Though they both have low partial pressures of hydrogen, the much higher residence time and lower temperatures can favor substantially more cracking of aromatic compounds in the coking vessel.

In conclusion, the catalytic cracking in the coking vessel in the exemplary embodiments of the present invention is substantially differentiated over the known art of fluid catalytic cracking. Various types of FCC catalyst (e.g. equilibrium, fresh, etc.) have been noted to be a type of catalyst that has the desired characteristics for various embodiments of the present invention. In this regard, the catalytic cracking and coking reactions of certain reactants (e.g. HCGO) are expected to have similar characteristics. However, the basic reactor design and reaction conditions are substantially different.

Utility of Exemplary Embodiments of the Present Invention: Refinery computer optimization models can be used to establish the utility of various exemplary embodiments of the present invention. Most refineries currently use refinery optimization models (e.g. LP Models) to optimize refinery process operations to maximize profit (or other objectives), based on the refinery process scheme, refinery crude blend, and market values for final products. The optimization model typically contains individual models for each refinery process in its refinery process scheme to assess the optimal operation to best utilize its capabilities and capacity. These refinery models typically estimate values of various process streams, including the feed and products of a coking process. In some models, the value of the 'internal recycle' in some exemplary embodiments of the present invention of a coking process can be valued based on its effects on process capacity and associated products. These values are typically generated in a dollars per barrel basis (i.e. $/Bbl.), but can be readily converted to cents per pound (c/Lb.), as well. Typically, the relative rankings (lowest to highest value in c/Lb) of the coker process streams are as follows: coke (lowest), recycle, feed, refinery fuel gas, HCGO, LCGO, Naphtha, LPGs, and gaseous olefins (highest). The HCGO, LCGO, and naphtha values are comparable and actually can have different relative rankings from refinery to refinery, due to differences in refinery process scheme and refinery crude blend. For example, the FCC capacity and/or capacities of downstream processing units for LCGO and naphtha can have effects on their relative values. In refineries where the FCC capacity is limited, opportunities may exist to use an exemplary embodiment of the present invention to use the coking process as incremental capacity for cracking HCGO to LCGO, naphtha, and lighter components. In many refineries, the refinery fuel gas value is often over ten times higher in value than the coke, and the other process streams are valued at 15 to 20 times higher. Consequently, most exemplary embodiments of the present invention that crack high boiling point materials that would otherwise form coke have very high utility. An exception to this general rule exists in refineries where coking small portions of HCGO or heavier material can improve operations of coking process or downstream processes (e.g. FCC due to better quality HCGO), and provide greater value. In addition, an exemplary embodiment of the present invention that cokes undesirable materials in the HCGO can lead to improvement of coke quality and sufficiently leverage the coke value, while improving HCGO quality to reduce operating problems in downstream processing equipment (e.g. FCC).

In conclusion, the most favorable exemplary embodiment of the present invention will depend on its economic or upgrade value. In many refineries, the highest product upgrade value will be cracking the highest boiling point materials that would otherwise form coke. Thus, exemplary embodiments of the present invention that produce less coke and more liquids may provide the best upgrade value.

Use of Olefin Production Characteristics of Catalyst to Increase Low Boiling Point Olefins: Another exemplary embodiment of the present invention is the use of the olefin production from newly developed and/or existing types of catalysts to increase the production of light olefins (e.g. ethylene, propylenes, butylenes, pentenes) for alkylation process unit feed, the production of oxygenates, and petrochemical feedstocks, such as plastics manufacture. Currently, many refineries have sufficient production of these lighter olefins and a sufficient market (e.g. local) or process scheme (e.g. alkylation unit) to justify separating these light olefins from refinery fuel gas or liquid petroleum gas (LPG) fractions. In other refineries, a substantial increase in the production of these olefins would be sufficient to justify the addition of such separation equipment due to the high value of these petrochemical feedstocks. Thus, the production of lighter olefins in gaseous products of the coking process would increase the value or utility of the current invention in this exemplary embodiment.

Similar to other exemplary embodiments, the injection of a catalytic additive in the coking process (preferably in the coking vessel in many exemplary embodiments of the invention) would be used to optimize the olefin production with existing types of acid catalysts (including but not limited to traditional Fluid Catalytic Cracking Unit (FCCU) catalysts in traditional oil refineries). Typically, a low activity catalyst can be used to provide sufficient acid density for cracking, but maintain a lower hydrogen activity level to preferentially produce olefins over parafins. However, it is anticipated that new catalysts could also be developed to enhance (or maximize) the quantity of olefins produced in the gas production of the coking process for a given feed or injection level of the catalytic additive.

This exemplary embodiment of the present invention is an improvement over the present invention described in the priority document. That is, this exemplary embodiment of the present invention would represent a new benefit (with results not expected in the coking process) from an existing catalyst already described previously, and not necessarily require the development or use of a new catalyst formulation. However, the development of a new catalyst formulation for this specific function may provide even greater utility, particularly in applications where incremental olefins would justify the appropriate separation equipment. This exemplary embodiment of the present invention would be more useful in refineries that are geared for higher production of petrochemical feedstocks.

Use of Olefin Production Characteristics of a Catalyst to Improve Coker Naphtha Quality: Another exemplary embodiment of the present invention is the use of the olefin production from newly developed and/or existing types of catalysts to improve the coker naphtha quality. Currently, the coker naphtha in many refineries is lower value than some other naphtha process streams in the refinery because of its lower octane level (due to its lower olefin or aromatic content). As such, the coker naphtha may need to be treated further in an isomerization unit, catalytic reformer, or other process unit to raise its octane level for gasoline blending. Otherwise, the coker naphtha is blended with more costly components in the gasoline pool or used in other, less valuable refinery products. Thus, the olefin production in the naphtha boiling range (e.g. between 180 and 400 degrees Fahrenheit) would increase the value or utility of the current invention in this exemplary embodiment.

Similar to other exemplary embodiments, the injection of a catalytic additive in the coking process (preferably in the coking vessel in many exemplary embodiments of the invention) would be used to optimize the olefin production with existing types of acid catalysts (including but not limited to traditional Fluid Catalytic Cracking Unit (FCCU) catalysts in traditional oil refineries). Typically, a low activity catalyst can be used to provide sufficient acid density for cracking, but maintain a lower hydrogen activity level to preferentially produce olefins over parafins. However, it is anticipated that new catalysts could also be developed to enhance (or maximize) the quantity of olefins produced in the naphtha boiling range for a given feed or injection level of the catalytic additive. In a similar manner, a catalyst could be developed to optimize the combination of olefins and/or aromatics to increase the octane levels without exceeding the individual environmental limits on olefins or aromatics.

This exemplary embodiment of the present invention is an improvement over the present invention described in the priority document. That is, this exemplary embodiment of the present invention would represent a new benefit (with results not expected in the coking process) from an existing catalyst already described previously, and not necessarily require the development or use of a new catalyst formulation. However, the development of a new catalyst for this specific function may provide even greater utility, particularly in applications where incremental olefins would make the resulting naphtha a gasoline blending component that does not require further processing. This exemplary embodiment of the present invention would be more useful in refineries (e.g. U.S.) that are geared for higher production of transportation fuels.

Use of Cracking Characteristics of a Catalyst to Optimize the Production of Heavy Coker Gas Oil, Light Coker Gas Oil and Naphtha: Another exemplary embodiment of the present invention is the use of the cracking characteristics of newly developed and/or existing types of catalysts to optimize the production of light gas oils and naphtha from the coking process. As stated previously, refinery optimization computer models are often used to establish the optimal process conditions to maximize profits (or other objective. As such, these computer models (e.g. LP models) establish the values for the heavy coker gas oil (HCGO), light coker gas oil (LCGO), naphtha, and other products of the coking process. These values are primarily based on the refinery process scheme, the crude blend, and product markets. As described above, the HCGO, LCGO, and naphtha values are comparable and actually can have different relative rankings from refinery to refinery due to differences in refinery process scheme and refinery crude blend. Adjusting the catalyst formulation to optimize the yields of HCGO, LCGO, and naphtha according to each refinery's computer optimization model would increase the value or utility of the current invention in this exemplary embodiment. In addition, opportunities may exist In refineries where the FCC capacity is limited to use an exemplary embodiment of the present invention to use the coking process as incremental capacity for cracking HCGO to LCGO, naphtha, and lighter components.

Similar to other exemplary embodiments, the injection of a catalytic additive in the coking process (preferably in the coking vessel in many exemplary embodiments of the invention) would be used to optimize the yields of HCGO, LCGO, and naphtha according to each refinery's computer optimization model with existing types of acid catalysts (including but not limited to traditional Fluid Catalytic Cracking Unit (FCCU) catalysts in traditional oil refineries). It is anticipated that new catalysts could also be developed to optimize the yields of HCGO, LCGO, and naphtha according to each refinery's computer optimization model.

This exemplary embodiment of the present invention is an improvement over the present invention described in the priority document. That is, this exemplary embodiment of the present invention would represent a new benefit (with results not expected in the coking process) from an existing catalyst already described previously, and not necessarily require the development or use of a new catalyst formulation. However, the development of a new catalyst for this specific function may provide even greater utility, particularly in applications where incremental cracking capacity of HCGO to LCGO and/or naphtha would relieve FCCU limits. This exemplary embodiment of the present invention would be more useful in refineries (e.g. U.S.) that are geared for higher production of transportation fuels.

Operation of the Invention: The operation of the equipment in FIG. 1 is straightforward, after the appropriate additive mixture has been determined. The components are added to the heated (e.g. steam coils), mixing tank (or other means of mixing and means of temperature regulation) with their respective quality and quantity as determined in previous tests (e.g. commercial demonstration). Whether the mixing is a batch or a continuous basis, the injection of the additive of this invention is added to the coking process at the predetermined points and times to achieve the desired reactions while the coking process proceeds. For example, continuous injection is often preferable (but not required) may occur in the drums that are in the coking cycle in the semi-continuous process of the delayed coking. However, in these cases, injection at the beginning and end of the coking cycles may not be preferable due to warm up and antifoam issues. Preferably, the flow rate of the additive of the present invention may be proportional to the flow rate of the coking process feed (e.g. 1.5 wt. %) and can be adjusted accordingly as the coking process feed flow rate changes.

In the general exemplary embodiment, the additive package is designed to promote the desired reactions with the coker feed, intermediate chemical species, cracked liquids, vapor products, and/or other process streams in the coking process. This is primarily achieved by the choice of catalyst. The catalyst(s)' substrate and impregnated materials, activity, selectivity, conversion, efficiency, and/or porosity characteristics will determine the types of reactants (e.g. gas oils) and products (e.g. Naphtha and fuel gas) from the catalytic cracking in the coking process. For example, cracking catalysts that are traditionally used for cracking in fluid catalytic cracking units (e.g. Fluid Catalytic Cracking Unit or FCCU) can be very effective in an application to crack various hydrocarbon molecules into lighter 'cracked liquids'. Alternatively, residua cracking catalysts have a higher degree of mesoporosity and other characteristics that allow the large molecules of the high boiling point components to have better access to and from the catalyst's active cracking sites. In addition, the other components of the additive package can influence cracking reactions over coking reactions, as well. As described previously, it is anticipated that various catalysts will be designed for the purposes above, particularly catalysts to achieve greater selective cracking of the coker feed, intermediate chemical species, cracked liquids, vapor products, and/or other coker process streams. This would include cracking of higher boiling point hydrocarbons to lower boiling point hydrocarbons that leave the coking vessel as vapors and enter the downstream fractionator where said lower boiling point hydrocarbons are separated into lower boiling point hydrocarbon process streams that are useful in oil refinery product blending. These lower boiling point hydrocarbon process streams include naphtha, gas oils, gasoline, kerosene, jet fuel, diesel fuel, heating oil, liquid petroleum gases, and fuel gas.

In many cases, the achievement of additional selective cracking of the various coker process streams. to 'cracked liquids' products is worth the cost of fresh cracking catalyst versus spent or regenerated catalyst. This economic determination will depend on the chemical structures of the coker process streams.

In its preferred embodiment, this catalytic additive selectively cracks the heavier components of the coker feed or intermediate chemical species to produce additional cracked liquids, while reducing coke production, and/or quenching cracking reactions in the vapor to reduce gas production.

Working Examples of General Exemplary Embodiments:
In order to more thoroughly describe the present invention, the following working examples are presented. The data presented in these examples was obtained in a pilot-scale, batch coker system. The primary component of this pilot-scale coker system is a stainless steel cylindrical reactor with an internal diameter of 3.0 inches and a height of 39 inches. A progressive cavity pump transfers the coker feed from the heated feed tank with mixer to the preheater and coker reactor. The nominal feed charge for each test is 4000 to 5000 grams over a 4-5 hour period. The preheater and coker temperatures are electronically controlled in an insulated furnace to the desired set points. A back pressure controller is used to maintain the desired reactor pressure. This pilot-scale system was used to generate data to demonstrate the benefits of the current invention over the known art. That is, the injection of the catalyst additive into the coking vessel of the current invention and the addition of catalyst to the coker feed of the known art were compared to a common baseline with no catalyst.

Comparative Test Examples 1 and 2

Coker feed from a commercial refinery was used to generate data for 2 tests with equivalent amounts of catalyst B. The operating conditions and the test results are shown in the following table.

|  |  | Run Number | | | | | |
|---|---|---|---|---|---|---|---|
|  |  | 94 | 100 | vs.94 | CT-1 | vs.94 | vs.100 |
|  |  | | | Feed Blend | | | |
|  | Units | 100% Valero Vac Resid | 100% Valero Vac Resid | | Valero Vac CatB + Resid + AntiFoam | | |
|  | | Test Conditions | | | | | |
| Average Drum Pressure | psig | 18.4 | 19.6 | | 19.5 | | |
|  | | Average Drum Temperatures | | | | | |
| Coke drum inlet temp | °C. | 483 | 485 | | 487 | | |
| Coke drum lower/middle temp | °C. | 463 | 456 | | 457 | | |
| Coke drum top temp | °C. | 421 | 430 | | 427 | | |
| Material Fed to Reactor | grams | 4814 | 5000 | | 4543 | | |
| Time for Test | minutes | | 290 | | 270 | | |
| Average Feed Rate | g/min | | 17.2 | | 16.8 | | |
|  | | Injected at Top | Injected at Top | | Cat in Feed | | |
| Decanted Slurry Oil w/Anti-Foam | grams | 160 | 180 | 3.6% | | | |
| Catalyst System | | NA | B | | B | | |
| Catalyst Quantity (Wt. % of Slurry) | grams | 0.0 | 24.1 | 13.4% | No Cat Slurry | | |
| Catalyst Quantity (Wt. % of Feed) | grams | 0.0 | 24.1 | 0.5% | 21.9 | 0.5% | |
|  | | Test Results | | | | | |
| Material Fed to Reactor | grams | 4814 | 5000 | | 4543 | | |
|  | | Products | | | | | |
| Coke | grams | 1613 | 1584 | | 1672 | | |
| Liquid | grams | 2557 | 2783 | | 2323 | | |
| Gas (by difference) | grams | 644 | 633 | | 548 | | |
|  | | Product Yields | | | | | |
| Coke | Wt. % | 33.5% | 31.7% | −5.5% | 36.8% | 9.8% | 16.2% |
| Liquid | Wt. % | 53.1% | 55.7% | 4.8% | 51.1% | −3.7% | −8.1% |
| Gas | Wt. % | 13.4% | 12.7% | −5.4% | 12.1% | −9.9% | −4.8% |

In the foregoing table, the catalyst addition of the known art showed a substantial increase in coking and a significant reduction in liquid yields. In contrast, the injection of the catalytic additive of the present invention showed a substantial reduction in coke yield and a significant increase in liquids production. Thus, these tests clearly demonstrate differentiation of the present invention over the known art. As described above, these results are likely due to the major differences in the chemical and physical nature of the primary reactants, exposed to the catalyst.

Comparative Test Examples 2, 3, and 4

Similarly, the coker feed from the same commercial refinery was used to generate data for 3 tests with equivalent amounts of catalyst C. The operating conditions and the test results are shown in the following table.

DESCRIPTION AND OPERATION OF ALTERNATIVE EXEMPLARY EMBODIMENTS

Delayed Coking Process

There are various ways the present invention can improve the delayed coking process. A detailed description of how the invention is integrated into the delayed coking process is followed by discussions of its operation in the delayed coking process and alternative exemplary embodiments relative to its use in this common type of coking process.

Traditional Delayed Coking Integrated with the Present Invention

FIG. 2 is a basic process flow diagram for the traditional delayed coking process of the known art. Delayed coking is a

|  | Units | \[Run Number\] 94 | 108 | vs.94 | CT-2 | vs.94 | vs.108 | CT-3 | vs.94 | vs.108 |
|---|---|---|---|---|---|---|---|---|---|---|
|  |  |  |  |  | Feed Blend |  |  |  |  |  |
|  |  | 100% Valero Vac Resid | 100% Valero Vac Resid |  | Valero Vac Resid + CatC + AntiFoam |  |  | Valero Vac Resid + CatC + AntiFoam |  |  |
|  |  |  |  | Test Conditions |  |  |  |  |  |  |
| Average Drum Pressure | psig | 18.4 | 17.4 |  | 17.5 |  |  | 17.5 |  |  |
|  |  |  |  | Average Drum Temperatures |  |  |  |  |  |  |
| Coke drum inlet temp | °C. | 483 | 480 |  | 476 |  |  | 477 |  |  |
| Coke drum lower/middle temp | °C. | 463 | 455 |  | 455 |  |  | 455 |  |  |
| Coke drum top temp | °C. | 421 | 429 |  | 431 |  |  | 432 |  |  |
| Material Fed to Reactor | grams | 4814 | 4062 |  | 3952 |  |  | 3715 |  |  |
| Time for Test | minutes |  | 279 |  | 281 |  |  | 263 |  |  |
| Average Feed Rate | g/min |  | 14.6 |  | 14.1 |  |  | 14.1 |  |  |
|  |  | Injected at Top | Injected at Top |  | Cat in Feed |  |  | Cat in Feed |  |  |
| Decanted Slurry Oil w/Anti-Foam | grams | 160 | 139 | 3.4% |  |  |  |  |  |  |
| Catalyst System |  | NA | C |  | C |  |  | C |  |  |
| Catalyst Quantity (Wt. % of Slurry) | grams | 0.0 | 19.3 | 13.9% | No Cat Slurry |  |  | No Cat Slurry |  |  |
| Catalyst Quantity (Wt. % of Feed) | grams | 0.0 | 19.3 | 0.5% | 18.8 | 0.5% |  | 17.7 | 0.5% |  |
|  |  |  |  | Test Results |  |  |  |  |  |  |
| Material Fed to Reactor | grams | 4814 | 4062 |  | 3952 |  |  | 3715 |  |  |
|  |  |  |  | Products |  |  |  |  |  |  |
| Coke | grams | 1613 | 1309 |  | 1368 |  |  | 1279 |  |  |
| Liquid | grams | 2557 | 2273 |  | 2009 |  |  | 1896 |  |  |
| Gas (by difference) | grams | 644 | 480 |  | 575 |  |  | 540 |  |  |
|  |  |  |  | Product Yields |  |  |  |  |  |  |
| Coke | Wt. % | 33.5% | 32.2% | −3.8% | 34.62% | 3.3% | 7.4% | 34.43% | 2.7% | 6.9% |
| Liquid | Wt. % | 53.1% | 56.0% | 5.4% | 50.84% | −4.3% | −9.2% | 51.04% | −3.9% | −8.8% |
| Gas | Wt. % | 13.4% | 11.8% | −11.7% | 14.55% | 8.7% | 23.1% | 14.54% | 8.6% | 23.0% |

In the foregoing table, the catalyst addition of the known art showed a substantial increase in coking and a significant reduction in liquid yields. In contrast, the injection of the catalytic additive of the present invention showed a substantial reduction in coke yield and a significant increase in liquids production. Thus, these tests clearly demonstrate differentiation of the present invention over the known art. As described above, these results are likely due to the major differences in the chemical and physical nature of the primary reactants, exposed to the catalyst.

semi-continuous process with parallel coking drums that alternate between coking and decoking cycles. The present invention integrates one or more additive injection system(s) into the delayed coking process equipment. The operation with the present invention is similar, as discussed below, but significantly different.

In general, delayed coking is an endothermic reaction with the furnace supplying the necessary heat to complete the cracking and coking reactions in the coke drum. The exact mechanism of delayed coking is so complex that it is not possible to determine all the various chemical reactions that occur, but three distinct steps take place:
1. Partial vaporization and mild cracking of the feed as it passes through the furnace
2. Cracking of the vapor as it passes through the coke drum
3. Successive cracking and polymerization of the heavy liquid trapped in the drum until it is converted to vapor or coke.

In the coking cycle, coker feedstock is heated and transferred to the coke drum until full. Hot residua feed 10 (most often the vacuum tower bottoms) is introduced into the bottom of a coker fractionator 12, where it combines with condensed recycle. This mixture 14 is pumped through a coker heater 16, where the desired coking temperature (normally between 900.degree. F. and 950.degree. F.) is achieved, causing partial vaporization and mild cracking. Steam or boiler feed water 18 is often injected into the heater tubes to prevent the coking of feed in the furnace. Typically, the heater outlet temperature is controlled by a temperature gauge 20 that sends a signal to a control valve 22 to regulate the amount of fuel 24 to the heater. A vapor-liquid mixture 26 exits the heater, and a control valve 27 diverts it to a coking drum 28. Sufficient residence time is provided in the coking drum to allow thermal cracking and coking reactions to proceed to completion. By design, the coking reactions are "delayed" until the heater charge reaches the coke drums. In this manner, the vapor-liquid mixture is thermally cracked in the drum to produce lighter hydrocarbons, which vaporize and exit the coke drum. The drum vapor line temperature 29 (i.e. temperature of the vapors leaving the coke drum) is the measured parameter used to represent the average drum outlet temperature. Quenching media (e.g. Gas Oil) is typically added to the vapor line to quench vapors. Petroleum coke and some residuals (e.g. cracked hydrocarbons) remain in the coke drum. When the coking drum is sufficiently full of coke, the coking cycle ends. The heater outlet charge is then switched from the first coke drum to a parallel coke drum to initiate its coking cycle. Meanwhile, the decoking cycle begins in the first coke drum. Lighter hydrocarbons 38 are vaporized, removed overhead from the coking drums, and transferred to a coker fractionator 12, where they are separated and recovered. Coker heavy gas oil (HGO) 40 and coker light gas oil (LGO) 42 are drawn off the fractionator at the desired boiling temperature ranges: HGO: roughly 610-800.degree. F.; LGO: roughly 400-610.degree. F. The fractionator overhead stream, coker wet gas 44, goes to a separator 46, where it is separated into dry gas 48, water 50, and unstable naphtha 52. A reflux fraction 54 is often returned to the fractionator.

In the decoking cycle, the contents of the coking drum are cooled down, remaining volatile hydrocarbons are removed, the coke is drilled from the drum, and the coking drum is prepared for the next coking cycle. Cooling the coke normally occurs in three distinct stages. In the first stage, the coke is cooled and stripped by steam or other stripping media 30 to economically maximize the removal of recoverable hydrocarbons entrained or otherwise remaining in the coke. In the second stage of cooling, water or other cooling media 32 is injected to reduce the drum temperature while avoiding thermal shock to the coke drum. Vaporized water from this cooling media further promotes the removal of additional vaporizable hydrocarbons. In the final cooling stage, the drum is quenched by water or other quenching media 34 to rapidly lower the drum temperatures to conditions favorable for safe coke removal. After the quenching is complete, the bottom and top heads of the drum are removed. The petroleum coke 36 is then cut, typically by a hydraulic water jet, and removed from the drum. After coke removal, the drumheads are replaced, the drum is preheated, and otherwise readied for the next coking cycle.

The present invention can be readily integrated into the traditional, delayed coker system, both new and existing. As shown in FIG. 3, this process flow diagram shows the traditional delayed coking system of FIG. 2 with the addition of an example of the present invention. This simplified example shows the addition of a heated, mixing tank (210) (an exemplary means of mixing and a means of temperature regulation) where components of the present invention's additive can be blended: catalyst(s) (220), seeding agent(s) (222), excess reactant(s) (224), carrier fluid(s) (226), and/or quenching agent(s) (228). The mixed additive (230) is then injected into the one or more points in the delayed coking process via properly sized pump(s) (250) (an exemplary means of pressurized injection) and piping, preferably with properly sized injection nozzle(s) (260). In this case, the pump is controlled by a flow meter (270) with a feedback control system relative to the specified set point for additive flow rate. Said one or more points in the delayed coking process would include (but should not be limited to) a hot residua feed 10, the bottom of a coker fractionator 12, condensed recycle, feed/recycle mixture 14, a coker heater 16, a vapor-liquid mixture 26 which exits the heater, and any combination thereof. Also, the catalytic additive can be added to a coking vessel at or above where the feed enters said coking vessel. In addition, the catalytic additive can be injected into a coker feed line, a coker vapor line, a coker fractionator, a coker feed pump, a coker heater, or any combination thereof. Furthermore, the catalytic additive can be introduced before a coking cycle, during a coking cycle, after a coking cycle, or any combination thereof.

Process Control of Traditional Delayed Coking with the Present Invention

In traditional delayed coking, the optimal coker operating conditions have evolved through the years, based on much experience and a better understanding of the delayed coking process. Operating conditions have normally been set to maximize (or increase) the efficiency of feedstock conversion to cracked liquid products, including light and heavy coker gas oils. More recently, however, the cokers in some refineries have been changed to maximize (or increase) coker throughput.

In general, the target operating conditions in a traditional delayed coker depend on the composition of the coker feedstocks, other refinery operations, and coker design. Relative to other refinery processes, the delayed coker operating conditions are heavily dependent on the feedstock blends, which vary greatly among refineries (due to varying crude blends and processing schemes or scenarios). The desired coker products and their required specifications also depend greatly on other process operations in the particular refinery. That is, downstream processing of the coker liquid products typically upgrades them to transportation fuel components. The target operating conditions are normally established by linear programming (LP) models that optimize the particular refinery's operations. These LP models typically use empirical data generated by a series of coker pilot plant studies. In turn, each pilot plant study is designed to simulate the particular refinery's coker design. Appropriate operating conditions are determined for a particular feedstock blend and particular product specifications set by the downstream processing requirements. The series of pilot plant studies are typically designed to produce empirical data for operating conditions with variations in feedstock blends and liquid product specification requirements. Consequently, the coker designs and target operating conditions vary significantly among refineries.

In common operational modes, various operational variables are monitored and controlled to achieve the desired delayed coker operation. The primary independent variables are feed quality, heater outlet temperature, coke drum pressure, and fractionator hat temperature. The primary dependent variables are the recycle ratio, the coking cycle time and the drum vapor line temperature. The following target control ranges are normally maintained during the coking cycle for these primary operating conditions:
1. Heater outlet temperatures in range of about 900.degree. F. to about 950.degree. F.,
2. Coke drum pressure in the range of about 15 psig to 100 psig: typically 15-25 psig,
3. Hat Temperature: Temperature of vapors rising to gas oil drawoff tray in fractionator
4. Recycle Ratio in the range of 0-100%; typically 10-20%
5. Coking cycle time in the range of about 12 to 24 hours; typically 15-20 hours
6. Drum Vapor Line Temperature 50 to 100.degree. F. less than the heater outlet temperature: typically 830-900 degrees Fahrenheit.
These traditional operating variables have primarily been used to control the quality of the cracked liquids and various yields of products. Throughout this discussion, "cracked liquids" refers to hydrocarbon vapor products of the coking process that have 5 or more carbon atoms. They typically have boiling ranges between 97 and 870.degree. F., and are liquids at standard conditions. Most of these hydrocarbon products are valuable transportation fuel blending components or feedstocks for further refinery processing. Consequently, cracked liquids are normally the primary objective of the coking process.

Over the past ten years, some refineries have switched coker operating conditions to maximize (or increase) the coker throughput, instead of maximum efficiency of feedstock conversion to cracked liquids. Due to processing heavier crude blends, refineries often reach a limit in coking throughput that limits (or bottlenecks) the refinery throughput. In order to eliminate this bottleneck, refiners often change the coker operating conditions to maximize (or increase) coker throughput in one of three ways:
1. If coker is fractionator (or vapor) limited, increase drum pressure (e.g. 15 to 20 psig.)
2. If coker is drum (or coke make) limited, reduce coking cycle time (e.g. 16 to 12 hours)
3. If coker is heater (or feed) limited, reduce coker recycle (e.g. 15 wt. % to 12 wt. %)
All three of these operational changes increase the coker throughput. Though the first two types of higher throughput operation reduce the efficiency of feedstock conversion to cracked liquids (i.e. per barrel of feed basis), they can maximize (or increase) the overall quantity (i.e. barrels) of cracked liquids produced. These operational changes also tend to increase coke yield and coke VCM. However, any increase in drum pressure or decrease in coker cycle time is usually accompanied by a commensurate increase in heater outlet and drum vapor line temperatures to offset (or limit) any increases in coke yield or VCM. In contrast, the reduction in recycle is often accomplished by a reduction in coke drum pressure and an increase in the heavy gas oil end point (i.e. highest boiling point of gas oil). The gas oil end point is controlled by refluxing the trays between the gas oil drawoff and the feed tray in the fractionator with partially cooled gas oil. This operational mode increases the total liquids and maintains the efficiency of feedstock conversion to cracked liquids (i.e. per barrel of feed basis). However, the increase in liquids is primarily highest boiling point components (i.e. 'heavy tail') that are undesirable in downstream process units. In this manner, ones skilled in the art of delayed coking can adjust operation to essentially transfer these highest boiling point components to either the recycle (which reduces coker throughput) or the 'heavy tail' of the heavy gas oil (which decreases downstream cracking efficiency). The present invention provides the opportunity to (1) increase coker throughput (regardless of the coker section that is limiting), (2) increase liquid yields, (3) reduce coke yield, (4) reduce gas production, and/or (5) substantially reduce highest boiling point components in either recycle, heavy gas oil, or both. In this manner, each application of the present invention may determine which process is preferable to reduce the undesirable, highest boiling point components.

Impact of Present Invention on Delayed Coking Process

There are various ways the present invention can improve existing or new delayed coking processes in crude oil refineries and upgrading systems (e.g. shale oil, tar sands, bitumen, etc) for synthetic crudes. These novel improvements include, but should not be limited to, (1) improving a quantity of a coker product or the overall yield distributions of coker products, (2) improving a quality or a property of one or more of the coker products, (3) improving operation, maintenance, throughput capacity, efficiency, and/or processing alternatives of the coking process, (4) improving the operation, maintenance, throughput capacity, efficiency, and/or processing alternatives for other refinery processing units (5) catalytic cracking and/or coking of heavy aromatics in a manner that promotes sponge coke morphology and reduces 'hotspots' in coke cutting, (6) quenching drum outlet gases that reduce 'vapor overcracking', (7) debottlenecking all major sections of the delayed coking process (i.e. heater, drum, & fractionator sections), via reducing coker recycle, coke production, and vapor loading of fractionator, and/or (8) provide incremental catalytic cracking capacity for a crude oil refinery or upgrading system.

In all the examples for delayed coking processes, the present invention provides the opportunity to develop catalytic additive(s) to address the specific needs of the particular refinery. That is, the catalytic additive(s) can be specifically designed to improve the qualities or yield distribution of the products that are most valuable to that refinery's process scheme and crude slate opportunities. This approach may simply involve catalytic cracking to produce greater yields of cracked liquids or may involve more sophisticated catalytic additive to be selective in what types of cracked liquids predominate. Similarly, an additional catalytic additive could be added to produce more of the desired products at that particular facility (e.g. propylene for local plastics plant). In this approach, the process optimization model in each refinery could be used as an effective tool in determining what catalytic additives would be preferable and worth pursuing (e.g. cost effectiveness and return on investment).

In many of the delayed coking process applications of the present invention, an exemplary embodiment of the present invention can achieve one or more of the following: (1) improved coker gas oil quality, (2) improved coke quality and market value, (3) less gas production, (4) less coke production, (5) increased coker and refinery capacities, (6) increased use of cheaper, lower quality crudes and/or coker feeds, (7)

increased efficiency and run time of downstream cracking units, (8) decreased operation & maintenance cost of coker and downstream cracking units, (9) reduced incidents of 'hotspots' in pet coke drum cutting, and/or (10) reduced catalyst make-up and emissions in downstream cracking units.

The following examples provide illustrative applications of the current invention. These examples are classified by coke quality and market, since the quality and quantity of catalyst additive can be restricted by the type of coke and its product specifications for its corresponding market.

Example 1

In fuel grade coke applications, the delayed coking feedstocks are often residuals derived from heavy, sour crude, which contain higher levels of sulfur and metals. As such, the sulfur and metals (e.g. vanadium and nickel) are concentrated in the pet coke, making it usable only in the fuel markets. Typically, the heavier, sour crudes tend to cause higher asphaltene content in the coking process feed. Consequently, the undesirable 'heavy tail' components (e.g. PAHs) are more prominent and present greater problems in downstream catalytic units (e.g. cracking). In addition, the higher asphaltene content (e.g. >15 wt. %) often causes a shot coke crystalline structure, which can cause coke cutting 'hot spots' and difficulties in fuel pulverization.

In addition to the previously described benefits for all delayed coking systems, the present invention further provides the selective cracking and coking of the 'heavy tail' components (e.g. PAHs) in coker gas oil of the traditional delayed coking process. Gas oil end points may be selectively reduced from over 1050 degrees of Fahrenheit to 1000 degrees of Fahrenheit or less (e.g. preferably <950 degrees of Fahrenheit) With greater amounts of additive, additional heavy components of the heavy coker gas oil and the coker recycle can be selectively cracked or coked. This improves coker gas oil quality/value and the performance of downstream cracking operations. In addition, the selective cracking of PAHs and quench (thermal & chemical) of the vapor overcracking improves the value of the product yields and increases the 'cracked liquids' yields. Also, the reduction of heavy components that have a high propensity to coke reduces the buildup of coke in the vapor lines and allows the reduction of recycle and heater coking.

In some applications, the heavy gas oil quality can deteriorate due to excessive cracking of heavier components that would otherwise form coke. Sufficient cracked liquids from these heavier components can still cause a net increase in the heavy gas oil endpoint. However, sufficient reduction in coke production can be still worth an increase in gas oil endpoint or an increase in recycle to reduce gas oil endpoint. In many cases, the delayed coker is coke drum limited, which allows additional recycle without limiting capacity. This additional recycle may allow the refinery to maintain or improve gas oil endpoint through sufficient recycle. At the same time, the coker throughput capacity (and refinery throughput capacity) may increase due to less coke production in a drum limited coker, while gaining additional profitability of increased cracked liquids.

With a properly designed catalytic additive package (e.g. catalyst & excess reactants), the present invention may also be effectively used to alleviate problems with 'hot spots' in the coke drums of traditional delayed coking. That is, the heavy liquids that remain in the pet coke, block coke quenching channels, and cause the 'hot spots' during the decoking cycle (e.g. coke cutting) are encouraged to further crack (preferable) or coke by the catalyst and excess reactants in the additive package. To this end, catalyst(s) and excess reactant(s) for this purpose can include, but should not be limited to, FCCU catalysts, hydrocracker catalysts, activated carbon, crushed coke, FCCU slurry oil, FCCU cycle oils, and coker heavy gas oil.

In fuel grade applications, the choice of catalyst(s) in the additive package has greater number of options, since the composition of the catalyst (e.g. metals) is less of an issue in fuel grade pet coke specifications (e.g. vs. anode). Thus, the catalyst can contain substrates and exotic metals to preferentially and selectively crack (vs. coke) various coker feed components, intermediate chemical species, and gas oil components, including the undesirable, heavy hydrocarbons (e.g. PAHs). Again, catalyst(s) and excess reactant(s) for this purpose may include, but should not be limited to, FCCU catalysts, hydrocracker catalysts, iron, activated carbon, crushed coke, FCCU slurry oil, and coker heavy gas oil. The most cost effective catalyst(s) may include spent or regenerated catalysts from downstream units (e.g. FCCU, hydrocracker, and hydrotreater) that have been sized and injected in a manner to prevent entrainment in coking process product vapors to the fractionator. In fact, the nickel content of hydrocracker or FCCU spent catalyst may be very effective in selectively coking the undesirable, heavy components (e.g. PAHs) of coker gas oil. The following example is given to illustrate a cost effective source of catalyst for the present invention. A certain quantity of FCCU equilibrium catalyst of the FCCU is normally disposed of on a regular basis (e.g. daily) and replaced with fresh FCCU catalyst to keep activity levels up. The equilibrium catalyst is often regenerated prior to disposal and could be used in the present invention to crack feed components, intermediate chemical species, cracked liquids, vapor products, or other coking process streams. particularly if the FCCU catalyst is designed to handle residua in the FCCU feed. If the equilibrium catalyst does not provide sufficient cracking catalyst activity, it could be blended with a new catalyst (e.g. catalyst enhancer) to achieve the desired activity while maintaining acceptable catalyst costs. Finally, certain new catalysts may be cost effective, as well.

When applied to greater degrees, the present invention can also be used to improve the coke quality while improving the value of coke product yields and improved operations and maintenance of the coker and downstream units. That is, the Hardgrove Grindability Index (HGI) of the coke can be increased to improve pulverization characteristics and market value. HGI values of greater than 50 (preferably 55 to 80) are possible. Likewise, the heating value can be increased by up to 10% and the Volatile Materials (VM with theoretical boiling points >950 degrees Fahrenheit but <1780 degrees Fahrenheit) from 12 to 25 wt. % (preferably 13 to 18 wt. %) of the fuel grade coke can also be increased to improve the fuel quality. In this manner, increasing the quality and/or quantity of catalytic additive(s) may incrementally improve return on investment according to the particular refinery's LP model.

In this example, the current invention may also provide incremental catalytic cracking capacity for a crude oil refinery or upgrading system (e.g. shale oil, tar sands, bitumen, etc.). That is, additional catalytic cracking in some coking process applications can provide a cost-effective alternative to adding or debottlenecking downstream cracking units. To allow more effective use of the catalysts, cyclones (similar to those used in FCCUs) could be retrofitted in the top of the coke drum to avoid entrainment of catalyst in the product vapors.

Example 2

In addition to the previously described benefits for all delayed coking systems, the present invention may provide additional utility for various types of anode grade facilities: (1) refineries that currently produce anode coke, but want to add opportunity crudes to their crude blends to reduce crude costs and (2) refineries that produce pet coke with sufficiently low sulfur and metals, but shot coke content is too high for anode coke specifications. In both cases, the present invention can be used to reduce shot coke content to acceptable levels, even with the presence of significant asphaltenes (e.g. >15 wt. %) in the coker feed.

With the present invention, refineries that currently produce anode quality coke can potentially add significant levels of heavy, sour opportunity crudes (e.g. >5 wt. %) without causing shot coke content higher than anode coke specifications. That is, the present invention can be used to convert feed components, intermediate chemical species, cracked liquids, and/or product vapors in a manner that preferably produces sponge coke crystalline structure (coke morphology) rather than shot coke crystalline structure. Thus, these refineries can reduce crude costs without sacrificing anode quality coke and its associated higher values.

With the present invention, refineries that currently produce shot coke content above anode coke specifications can reduce shot coke content to acceptable levels in many cases. That is, the present invention converts feed components, intermediate chemical species, cracked liquids, and/or product vapors in a manner that preferably produces sponge coke crystalline structure (coke morphology) rather than shot coke crystalline structure. Thus, these refineries can increase the value of its petroleum coke while maintaining or improving coker product yields and coker operation and maintenance.

In both anode coke cases, the additive package must be designed to minimize any increases in the coke concentrations with respect to sulfur, nitrogen, and metals that would add impurities to the aluminum production process. Thus, the selection of catalyst(s) is less flexible for these cases and would likely include alumina or carbon based (e.g. activated carbon or crushed coke) catalyst substrates. In both anode coke cases, the additive package must be designed to minimize the increase in VCMs and/or preferably produce additional VCMs with theoretical boiling points greater than 1250 degrees Fahrenheit. Thus, catalyst(s) and excess reactants for this additive package would be selected to promote the preferential production of sponge coke with higher molecular weights in the coking vessel. With this additive package, catalytic coking, thermal coking, and/or significant polymerization of feed components, intermediate chemical species, cracked liquids, and/or product vapors and the excess reactants produces a porous, sponge coke that has acceptable quality for calcining.

In these cases, an optimal level of VCMs greater than 1250 degrees Fahrenheit may be desirable to (1) provide volatilization downstream of the upheat zone in the coke calciner and (2) cause recoking of these volatile materials in the internal pores of the calcined coke to increase coke density. The resulting calcined coke will preferably have a substantially greater vibrated bulk density and require less pitch binder to be adsorbed in the coke pores to produce acceptable anodes for aluminum production facilities. In this manner, a superior anode coke may be produced that lowers anode production costs and improves their quality. Beyond this optimal level of VCMs greater than 1250 degrees Fahrenheit, any coke produced by the present invention will preferably not contain any VCMs. That is, any further coke produced will all have theoretical boiling points greater than 1780 degrees Fahrenheit, as determined by the ASTM test method for VCMs.

Example 3

In addition to the previously described benefits for all delayed coking systems, the present invention may provide additional utility for various types of needle coke facilities. In needle coke applications, the coking process uses special coker feeds that preferably have high aromatic content, but very low asphaltene content. These types of coker feeds are necessary to achieve the desired needle coke crystalline structure. These delayed coker operations have higher than normal heater outlet temperatures and recycle rates. With the present invention, these coking processes may maintain needle coke crystalline structure with higher concentrations of asphaltenes and lower concentrations of aromatics in the coker feed. The present invention may also reduce the recycle rate required to produce the needle coke crystalline structure with acceptable quality for electrodes, potentially increasing the coker capacity and improving coker operations and maintenance. In this manner, the present invention could decrease coker feed costs, while potentially increasing needle coke production and profitability.

Example 4

In addition to the previously described benefits for all delayed coking systems, the present invention may provide additional utility for various types of delayed coker facilities that produce specialty carbon products. Some delayed coker systems have the potential to produce petroleum coke for certain specialty carbon products, but do not due to economic and/or safety concerns. These specialty carbon products include (but should not be limited to) graphite products, electrodes, and steel production additives. The present invention allows improving the coke quality for these applications, while addressing safety concerns and improving economic viability. For example, certain graphite product production processes require a petroleum coke feed that has higher VCM content and preferably sponge coke crystalline structure. The present invention can be optimized to safely and economically produce the pet coke meeting the unique specifications for these applications. Furthermore, the quality of the VCMs may be adjusted to optimize the graphite production process and/or decrease process input costs.

Fluid Coking and Flexicoking Processes

Exemplary embodiments of the present invention may also provide significant improvements in other coking technologies, including the fluid coking and flexicoking processes. The flexicoking process is essentially the fluid coking process with the addition of a gasifier vessel for gasification of the petroleum coke. A detailed description of how the present invention is integrated into the fluid coking and flexicoking processes is followed by discussions of its operation in the fluid coking and flexicoking processes and alternative exemplary embodiments relative to its use in these types of coking processes.

Traditional Fluid Coking and Flexicoking Integrated with the Present Invention

FIG. 4 shows a basic process flow diagram for a traditional, fluid coking process. The flexicoking process equipment is essentially the same, but has an additional vessel for the gasification of the product coke 178 (remaining 75 to 85% of the coke that is not burned in the Burner 164). Fluid coking is a continuous coking process that uses fluidized solids to further increase the conversion of coking feedstocks to cracked liquids, and reduce the volatile content of the product coke. Fluid coking uses two major vessels, a reactor 158 and a burner 164.

In the reactor vessel 158, the coking feedstock blend 150 is typically preheated to about 600 to 700 degree F., combined with the recycle 156 from the scrubber section 152, where vapors from the reactor are scrubbed to remove coke fines. The scrubbed product vapors 154 are sent to conventional fractionation and light ends recovery (similar to the fractionation section of the delayed coker). The feed and recycle mixture is sprayed into the reactor 158 onto a fluidized bed of hot, fine coke particles. The mixture vaporizes and cracks, forming a coke film (about 0.5 um) on the particle surfaces. Since the heat for the endothermic cracking reactions is supplied locally by these hot particles, this permits the cracking and coking reactions to be conducted at higher temperatures of about 510.degree. C.-565.degree. C. or (950.degree. F.-1050.degree. F.) and shorter contact times (15-30 seconds) versus delayed coking. As the coke film thickens, the particles gain weight and sink to the bottom of the fluidized bed. High-pressure steam 159 is injected via attriters and break up the larger coke particles to maintain an average coke particle size (100-600 um), suitable for fluidization. The heavier coke continues through the stripping section 160, where it is stripped by additional fluidizing media 161 (typically steam). The stripped coke (or cold coke) 162 is then circulated from the reactor 158 to the burner 164.

In the burner, roughly 15-25% of the coke is burned with air 166 in order to provide the hot coke nuclei to contact the feed in the reactor vessel. This coke burn also satisfies the process heat requirements without the need for an external fuel supply. The burned coke produces a low heating value (20-40 Btu/scf) flue gas 168, which is normally burned in a CO Boiler or furnace. Part of the unburned coke (or hot coke) 170 is recirculated back to the reactor to begin the process all over again. A carrier media 172, such as steam, is injected to transport the hot coke to the reactor vessel. In some systems, seed particles (e.g. ground product coke) must be added to these hot coke particles to maintain a particle size distribution that is suitable for fluidization. The remaining product coke 178 must be removed from the system to keep the solids inventory constant. It contains most of the feedstock metals, and part of the sulfur and nitrogen. Coke is withdrawn from the burner and fed into the quench elutriator 174 where product coke (larger coke particles) 178 are removed and cooled with water 176. A mixture 180 of steam, residual combustion gases, and entrained coke fines are recycled back to the burner.

The present invention may be readily integrated into the traditional, flexicoking and fluid coking systems, both new and existing. As shown in FIG. 5, this process flow diagram shows the traditional flexicoking system of FIG. 4 with the addition of an example of the present invention. This simplified example shows the addition of a heated, mixing tank (210) (as an exemplary means of mixing and means of controlling temperature) where components of the present invention's additive can be blended: catalyst(s) (220), seeding agent(s) (222), excess reactant(s) (224), carrier fluid(s) (226), and/or quenching agent(s) (228). Obviously, if the additive package is comprised of only one or two of these components, the need for a heated, mixing tank or other means of mixing and temperature control can be reduced or eliminated. The mixed additive (230) is then injected into one or more points in the flexicoking and fluid coking systems via properly sized pump(s) (250) (as an exemplary means of pressurized injection) and piping, preferably with properly sized injection nozzle(s) (260). In this case, the pump is controlled by a flow meter (270) with a feedback control system relative to the specified set point for additive flow rate. Said one or more points in the flexicoking and fluid coking may include, but should not be limited to, coking process feed blend 150, coking process reactor vessel (e.g. coking Vessel) 158, coking process burner 164, coking process recycle 156, coking process scrubber system 152, scrubbed product vapors 154, recirculated hot coke 170, or any combination thereof.

B. Process Control of the Known Art

In traditional fluid coking, the optimal operating conditions have evolved through the years, based on much experience and a better understanding of the process. Operating conditions have normally been set to maximize (or increase) the efficiency of feedstock conversion to cracked liquid products, including light and heavy coker gas oils. The quality of the byproduct petroleum coke is a relatively minor concern.

As with delayed coking, the target operating conditions in a traditional fluid coker depend on the composition of the coker feedstocks, other refinery operations, and the particular coker's design. The desired coker products also depend greatly on the product specifications required by other process operations in the particular refinery. That is, downstream processing of the coker liquid products typically upgrades them to transportation fuel components. The target operating conditions are normally established by linear programming (LP) models that optimize the particular refinery's operations. These LP models typically use empirical data generated by a series of coker pilot plant studies. In turn, each pilot plant study is designed to simulate the particular coker design, and determine appropriate operating conditions for a particular coker feedstock blend and particular product specifications for the downstream processing requirements. The series of pilot plant studies are typically designed to produce empirical data for operating conditions with variations in feedstock blends and liquid product specification requirements. Consequently, the fluid coker designs and target operating conditions vary significantly among refineries.

In normal fluid coker operations, various operational variables are monitored and controlled to achieve the desired fluid coker operation. The primary operational variables that affect coke product quality in the fluid coker are the reactor temperature, reactor residence time, and reactor pressure. The reactor temperature is controlled by regulating (1) the temperature and quantity of coke recirculated from the burner to the reactor and (2) the feed temperature, to a limited extent. The temperature of the recirculated coke fines is controlled by the burner temperature. In turn, the burner temperature is controlled by the air rate to the burner. The reactor residence time (i.e. for cracking and coking reactions) is essentially the holdup time of fluidized coke particles in the reactor. Thus, the reactor residence time is controlled by regulating the flow and levels of fluidized coke particles in the reactor and burner. The reactor pressure normally floats on the gas compressor suction with commensurate pressure drop of the intermediate components. The burner pressure is set by the unit pressure balance required for proper coke circulation. It is normally controlled at a fixed differential pressure relative to the reactor. The following target control ranges are normally maintained in the fluid coker for these primary operating variables:

1. Reactor temperatures in the range of about 950.degree. F. to about 1050.degree. F.,
2. Reactor residence time in the range of 15-30 seconds,
3. Reactor pressure in the range of about 0 psig to 100 psig: typically 0-5 psig,
4. Burner Temperature: typically 100-200.degree. F. above the reactor temperature, These traditional operating variables have primarily been used to control the quality of the cracked liquids and various yields of products, but not the respective quality of the byproduct petroleum coke.

C. Process Control of the Present Invention

There are various ways the present invention can improve existing or new flexicoking and fluid coking processes in crude oil refineries and upgrading systems for synthetic crudes. These novel improvements include, but should not be limited to, (1) reducing coke production, (2) reducing gas production by quenching product vapors in a manner that reduce 'vapor overcracking,' (3) increasing cracked liquids, (4) improving coker gas oil quality, (5) improving coke quality, (6) debottlenecking the heater, and (7) reducing recycle and vapor loading of fractionator.

In all the examples for flexicoking and fluid coking processes, the present invention provides the opportunity to develop catalytic additive(s) to address the specific needs of the particular refinery. That is, the catalytic additive(s) can be specifically designed to improve the yield distribution to the products that are most valuable to that refinery's process scheme and crude slate opportunities. This approach may simply involve catalytic cracking to produce greater yields of cracked liquids or may involve more sophisticated catalytic additive to be selective in what types of cracked liquids predominate. Similarly, an additional catalytic additive could be added to produce more of the desired products at that particular facility (e.g. propylene for local plastics plant). In this approach, the process optimization model in each refinery could be used as an effective tool in determining what catalytic additives would be preferable and worth pursuing (e.g. cost effectiveness and return on investment).

In many flexicoking and fluid coking applications of the present invention, an exemplary embodiment of the present invention can achieve one or more of the following: (1) improved coker gas oil quality, (2) improved coke quality and market value, (3) less gas production, (4) less coke production, (5) increased coker and refinery capacities, (6) increased use of cheaper, lower quality crudes and/or coker feeds, (7) increased efficiency and run time of downstream cracking units, (8) decreased operation & maintenance cost of coker and downstream cracking units, and (10) reduced catalyst make-up and emissions in downstream cracking units.

Example 5

In the fluid coking and flexicoking processes, the coke formation mechanism and coke morphology are substantially different from the delayed coking process. Injection of a properly designed catalytic additive into the coking vessel would provide a fluidized cracking catalyst that would catalytically increase cracking of the coker feed and reduce the amount of coke production. With additional injection of a catalytic additive (primarily quenching agent) at the inlet to the scrubber would quench the vapor overcracking reaction and reduce gas production. The present invention would still tend to push the pet coke toward sponge coke morphology, but would have less impact on the resulting coke (compared to the delayed coking process). Also, the present invention would have less impact on the quantity and quality of the additional VCMs in the pet coke.

As noted previously, the catalyst of the additive of the present invention can be sized properly (100 to 600 microns) to promote the fluidization of the catalyst to increase the residence time of the catalyst in this system and reduce the amount of catalyst that would be needed for the same level of conversion.

CONCLUSION, RAMIFICATIONS, AND SCOPE OF THE INVENTION

Thus the reader will see that the coking process modifications of the current invention provide a highly reliable means to catalytically change the quantity and quality of the products of said coking processes. This novel coking process modification provides the following advantages over traditional coking processes and recent improvements: (1) Increased cracked liquids, (2) less coke production, (3) less gas production, (4) improved coker gas oil quality, (2) improved coke quality and market value, (5) increased coker and refinery capacities, (6) increased use of cheaper, lower quality crudes and/or coker feeds, (7) increased efficiency and run time of downstream cracking units, (8) decreased operation & maintenance cost of coker and downstream cracking units, (10) reduced catalyst make-up and emissions in downstream cracking units, and/or (11) incremental catalytic cracking capacity for a crude oil refinery or upgrading system.

While the above description contains many specificities, these should not be construed as limitations on the scope of the invention, but rather as an exemplification of one preferred embodiment thereof. Many other variations are possible. For example, different catalytic additives could be injected at different points in the coking process to achieve different objectives.

Accordingly, the scope of the invention may be determined not by the embodiment(s) illustrated, but by the appended claims and their legal equivalents.

What is claimed is:

1. A process comprising introducing an additive including cracking catalyst into a coking vessel during a coking cycle of a delayed coking process such that reactions are enhanced to further increase a production of olefins in said coking process.

2. A process of claim 1 wherein said additive is added to the vapors above a coking vapor-liquid interface in said coking vessel.

3. A process of claim 1 wherein said additive is added to said coking process by a means of pressurized injection.

4. A process of claim 1 wherein said additive comprises said cracking catalyst(s), alone or in combination with seeding agent(s), excess reactant(s), quenching agent(s), carrier fluid(s), or any combination thereof.

5. A process of claim 1 wherein said cracking catalyst substantially increases a proportion of an olefin in gases separated from said coking process.

6. A process of claim 1, wherein said olefins are selected from a group comprising ethylene, propylene, butylenes, pentenes, and any combination thereof.

7. A process of claim 1 wherein said cracking substantially increases a proportion of olefins in a naphtha boiling point range.

8. A process of claim 7 wherein said olefins have boiling points in the range between 180 and 400 degrees Fahrenheit.

9. A process of claim 1 wherein said cracking catalyst is developed to optimize the production of heavy coker gas oil, light coker gas oil, naphtha, and gases.

* * * * *